(12) United States Patent
Wierzbicki et al.

(10) Patent No.: US 12,239,304 B2
(45) Date of Patent: *Mar. 4, 2025

(54) BIOCOMPATIBLE BIOMEDICAL OCCLUSION DEVICE

(71) Applicant: THE TEXAS A&M UNIVERSITY SYSTEM, College Station, TX (US)

(72) Inventors: Mark A. Wierzbicki, College Station, TX (US); Duncan Maitland, College Station, TX (US); Matthew W. Miller, Carefree, AZ (US); Andrea D. Muschenborn, Bloomington, IN (US); Landon Nash, College Station, TX (US); Jason M. Szafron, Hamden, CT (US); Todd Landsman, College Station, TX (US)

(73) Assignee: THE TEXAS A&M UNIVERSITY SYSTEM, College Station, TX (US)

( * ) Notice: Subject to any disclaimer, the term of this patent is extended or adjusted under 35 U.S.C. 154(b) by 5 days.

This patent is subject to a terminal disclaimer.

(21) Appl. No.: 17/837,111

(22) Filed: Jun. 10, 2022

(65) Prior Publication Data
US 2022/0304667 A1    Sep. 29, 2022

Related U.S. Application Data

(63) Continuation of application No. 16/751,436, filed on Jan. 24, 2020, now Pat. No. 11,357,488, which is a
(Continued)

(51) Int. Cl.
*A61B 17/00* (2006.01)
*A61L 31/14* (2006.01)

(52) U.S. Cl.
CPC ........ *A61B 17/0057* (2013.01); *A61L 31/146* (2013.01); *A61B 2017/00606* (2013.01); *A61B 2017/00871* (2013.01)

(58) Field of Classification Search
CPC ............. A61L 2430/36; A61L 2400/16; A61L 31/146; A61B 2017/00871;
(Continued)

(56) References Cited

U.S. PATENT DOCUMENTS 5,846,261 A * 12/1998 Kotula ............. A61B 17/12122
606/213
5,976,174 A    11/1999 Ruiz
(Continued)

FOREIGN PATENT DOCUMENTS

CN    1091584 C    10/2002
CN    2714003 Y    8/2005
(Continued)

OTHER PUBLICATIONS

China Patent Office, Office Action mailed Dec. 5, 2019 in Chinese Patent Application No. 201680037004.4 (10 pages).
(Continued)

*Primary Examiner* — Jocelin C Tanner
(74) *Attorney, Agent, or Firm* — Trop, Pruner & Hu, P.C.

(57) ABSTRACT

A device for a tissue channel includes a device frame, a shape memory polymer foam segment coupled to the device frame, and an attachment structure coupled to the device frame. The device frame includes a proximal structure, a distal structure, and an intermediate structure coupled to the proximal structure and the distal structure. The proximal structure is configured to collapse to fit into a delivery structure and expand to block migration of the proximal structure. The distal structure is configured to collapse to fit into the delivery structure and expand to block migration of the distal structure. The intermediate structure is configured to fit in the tissue channel upon device deployment. The shape memory polymer foam segment is configured to compress to fit into the delivery structure and occlude the
(Continued)

channel. The attachment structure is configured to attach and detach the device from a delivery guide.

17 Claims, 12 Drawing Sheets

Related U.S. Application Data continuation of application No. 15/567,682, filed as application No. PCT/US2016/028789 on Apr. 22, 2016, now Pat. No. 10,555,737.

(60) Provisional application No. 62/151,863, filed on Apr. 23, 2015.

(58) Field of Classification Search
CPC .......... A61B 2017/00867; A61B 2017/00606; A61B 2017/00592; A61B 2017/00575; A61B 2017/00243; A61B 17/12031; A61B 17/0057; A61B 17/1204; A61B 17/12036
See application file for complete search history.

(56) References Cited

U.S. PATENT DOCUMENTS

| | | | |
|---|---|---|---|
| 6,123,715 | A | 9/2000 | Amplatz |
| 10,555,737 | B2 | 2/2020 | Wierzbicki et al. |
| 11,357,488 | B2* | 6/2022 | Wierzbicki ........ A61B 17/0057 |
| 2002/0068950 | A1 | 6/2002 | Corcoran et al. |
| 2003/0236533 | A1 | 12/2003 | Wilson et al. |
| 2005/0065547 | A1 | 3/2005 | Marino et al. |
| 2005/0113861 | A1 | 5/2005 | Corcoran et al. |
| 2006/0009785 | A1 | 1/2006 | Maitland et al. |
| 2006/0122646 | A1 | 6/2006 | Cochran et al. |
| 2007/0010851 | A1 | 1/2007 | Chanduszko et al. |
| 2010/0324585 | A1 | 12/2010 | Miles et al. |
| 2011/0144686 | A1 | 6/2011 | Wilson et al. |
| 2011/0144689 | A1 | 6/2011 | Isch et al. |
| 2012/0172973 | A1 | 7/2012 | Deckard et al. |
| 2012/0330342 | A1* | 12/2012 | Jones ............... A61B 17/12177 606/200 |
| 2013/0231684 | A1 | 9/2013 | Aurilia et al. |
| 2013/0253086 | A1 | 9/2013 | Wilson et al. |
| 2013/0253634 | A1 | 9/2013 | Wilson et al. |
| 2013/0317541 | A1 | 11/2013 | Singhal et al. |
| 2014/0371789 | A1 | 12/2014 | Hariton et al. |
| 2015/0039017 | A1 | 2/2015 | Cragg et al. |
| 2018/0132856 | A1 | 5/2018 | Wierzbicki et al. |

FOREIGN PATENT DOCUMENTS

| | | |
|---|---|---|
| CN | 101094614 A | 12/2007 |
| CN | 101185582 A | 5/2008 |
| CN | 101374477 A | 2/2009 |
| CN | 102046094 A | 5/2011 |
| CN | 102083493 A | 6/2011 |
| CN | 102612345 A | 7/2012 |
| CN | 103596508 A | 2/2014 |
| CN | 104039241 A | 9/2014 |
| EP | 2248486 A2 | 11/2010 |
| JP | 2012130735 A | 7/2012 |
| WO | 2005053547 A2 | 6/2005 |
| WO | 2009082479 A2 | 7/2009 |

OTHER PUBLICATIONS

China Patent Office, Office Action mailed Aug. 21, 2020 in Chinese Patent Application No. 201680037004.4 (18 pages).
China Patent Office, Office Action mailed Feb. 19, 2021 in Chinese Patent Application No. 201680037004.4 (16 pages).
European Patent Office, Communication Pursuant to Rules 70(2) and 70a(2) EPC mailed Jan. 8, 2019 in European Patent Application No. 16783914.1 (60 pages).
European Patent Office, Intention to Grant mailed Jan. 25, 2021 in European Patent Application No. 16783914.1 (60 pages).
Japan Patent Office, Notice of Reasons for Rejection mailed Jan. 8, 2019 in Japanese Patent Application No. 2018-506803 (8 pages).
Japan Patent Office, Notice of Reasons for Rejection mailed Mar. 17, 2020 in Japanese Patent Application No. 2018-506803 (10 pages).
Japan Patent Office, Office Action mailed Jan. 5, 2021 in Japanese Patent Application No. 2018-506803 (4 pages).
The International Searching Authority, International Search Report and the Written Opinion mailed Jul. 28, 2016 in International Application No. PCT/US2016/28789 (16 pages).
The International Searching Authority, Written Opinion of the International Searching Authority and the International Search Report mailed Nov. 21, 2016 in International Application No. PCT/US2016/50097 (7 pages).
Singhal et al., "Ultra Low Density and Highly Crosslinked Biocompatible Shape Memory Polyurethane Foams", Journal of Polymer Sciences B Polymer Physics, May 15, 2012; vol. 50, Issue 10, pp. 724-737.
Landsman et al., "Design and verification of a shape memory polymer peripheral occlusion device", Journal of the Mechanical Behavior of Biomedical Materials, Jun. 23, 2016, vol. 63, pp. 195-206.
Rodriguez et al., "Reticulation of low density shape memory polymer foam with an in vivo demonstration of vascular occlusion", Journal of the Mechanical Behavior of Biomedical Materials, vol. 40, Aug. 11, 2014, pp. 102-114.
Wierzbicki et al.; "Mechanical and in vitro evaluation of an experimental canine patent ductus arteriosus occlusion device", available on-line Dec. 21, 2015, pp. 156-167, Journal of the Mechanical Behavior of Biomedical Materials 59, Elsevier Ltd.

\* cited by examiner

BIOCOMPATIBLE BIOMEDICAL OCCLUSION DEVICE

PRIORITY CLAIM

This application is a continuation of U.S. patent application Ser. No. 16/751,436, filed Jan. 24, 2020, which is a continuation of U.S. patent application Ser. No. 15/567,682, filed Oct. 19, 2017, now U.S. Pat. No. 10,555,737, issued Feb. 11, 2020, which is a § 371 national stage of international application PCT/US2016/028789, filed Apr. 22, 2016, which claims priority to U.S. Provisional Patent Application No. 62/151,863 filed on Apr. 23, 2015 and entitled "BIOCOMPATIBLE BIOMEDICAL OCCLUSION DEVICE." The content of each of the above applications is hereby incorporated by reference.

TECHNICAL FIELD

The present disclosure relates to occlusion devices. In particular, it relates to occlusion devices for tissue channels.

BACKGROUND

In humans and animals, defects may form in tissues due to creation of a channel through a tissue wall or failure of a channel in a tissue wall to close. For example, the ductus arteriosus is a vessel connecting the pulmonary artery to the aorta in human and animal neonates, shunting blood flow around the developing lungs. The ductus arteriosus typically closes shortly after birth. However, in some individuals, the ductus arteriosus may stay open, leading to a defect known as patent ductus arteriosus (PDA). PDA may lead to clinical conditions such as cardiac arrhythmias, congestive heart failure, and pulmonary over-circulation. Other conditions or defects involving open tissue channels include patent foramen ovale, ventricular septal defects, and atrial septal defects. Previous attempts to seal these tissue defects have involved surgical ligation, an invasive procedure that may lead to complications.

BRIEF DESCRIPTION OF THE DRAWINGS

Features and advantages of embodiments of the present invention will become apparent from the appended claims, the following detailed description of one or more example embodiments, and the corresponding figures. Where considered appropriate, reference labels have been repeated among the figures to indicate corresponding or analogous elements.

DETAILED DESCRIPTION

Figure 1A:
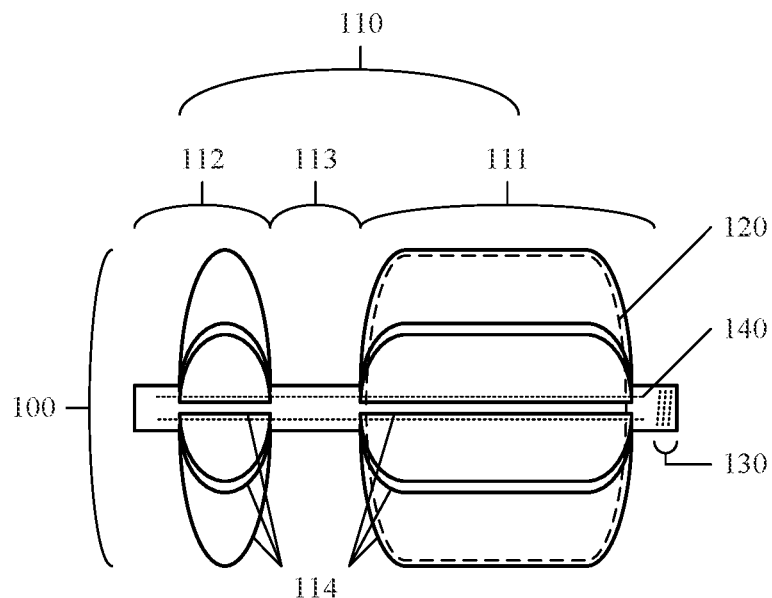
FIG. 1A is an exemplary diagram of a device having two sets of struts and a cylindrical proximal structure, and a discoid distal structure according to an embodiment.

Reference will now be made to the drawings wherein like structures may be provided with like suffix reference designations. In order to show the structures of various embodiments more clearly, the drawings included herein are diagrammatic representations of semiconductor/circuit structures. Thus, the actual appearance of the structures, for example in a photo, may appear different while still incorporating the claimed structures of the illustrated embodiments. Moreover, the drawings may only show the structures useful to understand the illustrated embodiments. Additional structures known in the art may not have been included to maintain the clarity of the drawings. "An embodiment", "various embodiments" and the like indicate embodiment(s) so described may include particular features, structures, or characteristics, but not every embodiment necessarily includes the particular features, structures, or characteristics. Some embodiments may have some, all, or none of the features described for other embodiments. "First", "second", "third" and the like describe a common object and indicate different instances of like objects are being referred to. Such adjectives do not imply objects so described must be in a given sequence, either temporally, spatially, in ranking, or in any other manner. "Connected" may indicate elements are in direct physical or electrical contact with each other and "coupled" may indicate elements co-operate or interact with each other, but they may or may not be in direct physical or electrical contact.

The disclosure includes a device and methods for making a device for a tissue channel having a proximal opening and a distal opening that includes a device frame, a shape memory polymer foam segment coupled to the device frame, and an attachment structure coupled to the device frame. The device frame has a central axis and includes a proximal structure, a distal structure, and an intermediate structure coupled to the proximal structure and the distal structure. The proximal structure is configured to collapse to fit into a delivery structure and expand to block migration of the proximal structure through the proximal opening. The distal structure is configured to collapse to fit into the delivery structure and expand to block migration of the distal structure through the distal opening. The intermediate structure is configured to fit in the tissue channel upon device deployment. The shape memory polymer foam segment coupled to the device and configured to compress to fit into the delivery structure and expand to occlude flow through the channel. The attachment structure is configured to attach and detach the device from a delivery guide.

According to embodiments of the disclosure, a device may be configured for minimally-invasive delivery into a tissue channel and secure occlusion of flow through the channel. This device may include an expandable frame configured to compress into a delivery structure and expand to secure the device into the tissue channel upon deployment. The device may have an expandable shape memory polymer foam segment coupled to the device and configured to expand and occlude flow through the channel. The device may have an attachment structure for attaching and detaching the device from a deployment mechanism.

For deployment, the device may be compressed into a delivery structure, such as a catheter. The delivery structure may be placed past the distal opening of the tissue channel and the device slowly pushed out of the delivery structure. As the device is removed from the delivery structure, a distal structure of the device frame may actuate and expand distal to the distal opening of the tissue channel. The device may be further extracted from the delivery structure, and a proximal structure of the device frame may actuate and expand proximal to the proximal opening of the tissue channel. The shape memory polymer foam segment may expand to an area equal to or greater than the area of the channel opening, obstructing flow through the channel. The device may be retracted and replaced until secured into the channel. After the device has been placed and secured within the tissue channel, the device may be detached from the attachment structure of the device and the delivery structure retracted from the body.

Device Frame

The device frame may be configured to compress into a delivery structure, expand into a predetermined shape, secure the device into a tissue channel, and prevent the device from becoming dislodged. The device frame may collapse to a compressed state to fit into a delivery structure. Upon deployment and/or actuation, proximal and distal structures of the device frame may be configured to expand and secure the device into the channel.

The device frame may include a proximal structure, a distal structure, and an intermediate structure. The proximal structure may correspond to the section of the device frame configured for placement at or proximal to the proximal opening of the tissue channel. The distal structure may correspond to the section of the device frame configured for placement at or distal to the distal opening of the tissue channel. The intermediate structure may correspond to the section of the device frame configured for placement within the channel. These structures may be fabricated from a single structure (monolithic) or multiple structures (non-monolithic). The device frame may also include external structures, such as radiopaque markers.

The device frame may contain radial support structures, such as elastic wires and struts, expanding radially from the device axis (spoke configuration). These radial support structures may be shaped and configured to compress and expand to a preconfigured shape. In addition to radial support, these radial support structures may run laterally down the proximal, distal, and intermediate structures to form cages. The radial support structures may be integrated as monolithic structures or coupled to radial coupling structures, such as backbone structures and end structures (hub configuration). The device frame may provide axial support for connecting the proximal and distal structures through an intermediate structure, such as continuous struts, a strut-free monolithic structure, or a backbone structure (axis configuration).

Monolithic Design

In embodiments of the disclosure, the device frame may be a monolithic design fabricated from a single, continuous material. For example, the proximal structure, distal structure, and intermediate structure may be formed from a single, continuous tube, where the struts are cut and positioned from the tube. In some embodiments, the proximal and distal structures each may have 2-30 struts.

Multiple Sets of Struts

Figure 1B:
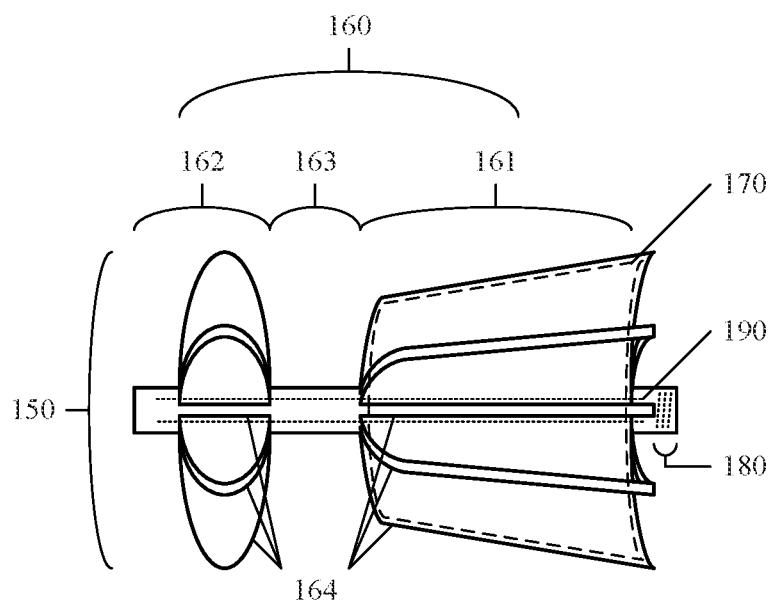
FIG. 1B is an exemplary diagram of a device having two sets of struts and a plug-shaped proximal structure, according to an embodiment.

In embodiments of the disclosure, the monolithic device frame may have a proximal structure made from at least a first set of struts and a distal structure made from a second set of struts. An intermediate structure may couple the proximal and distal structure. FIG. 1A and FIG. 1B are exemplary diagrams of monolithic device frames having two sets of struts, according to embodiments of the disclosure.

FIG. 1A is an exemplary diagram of a device 100 having two sets of struts and a cylindrical proximal structure, according to embodiments of the disclosure. The device 100 includes a monolithic device frame 110, a shape memory polymer foam segment 120, an attachment structure 130, and a backbone structure 140. The monolithic device frame 110 further includes a proximal structure 111, a distal structure 112, and an intermediate structure 113. The proximal structure 111 and the distal structure 112 are formed from two separate sets of struts 114 and coupled by the intermediate structure 113. The proximal structure 111 has a cylindrical shape, the distal structure 112 has a disc shape, and the shape memory polymer foam segment 120 has a cylindrical shape. The shape memory polymer foam segment 120 is coupled to the backbone structure 140 and contained within the proximal structure 111. The backbone structure 140 is coupled to the monolithic device frame 110 and position approximately along the central axis of the device 100. The attachment structure 130 is a segment on the monolithic device frame 110 that contains threads for attaching a threaded guide wire.

As a note, the backbone structure 140 does not need to go through the entire device in all embodiments. For example, backbone structure 140 may be present in only section 111, sections 111 and 113, or sections 111, 113, and 112.

FIG. 1B is an exemplary diagram of a device 150 having two sets of struts and a plug-shaped proximal structure, according to embodiments of the disclosure. The device 150 includes a monolithic device frame 160, a shape memory polymer foam segment 170, an attachment structure 180, and a backbone structure 190. The monolithic device frame 160 further includes a proximal structure 161, a distal structure 162, and an intermediate structure 163. The proximal structure 161 and the distal structure 162 are formed from two separate sets of struts 164 and coupled by the intermediate structure 163. The proximal structure 161 has a tapered plug shape, the distal structure 162 has a disc shape, and the shape memory polymer foam segment 170 has a tapered plug shape. The shape memory polymer foam segment 170 is coupled to the backbone structure 190 and contained within the proximal structure 171. The backbone structure 190 is coupled to the monolithic device frame 160 and positioned approximately along the central axis of the device 150. The attachment structure 180 is a segment on the monolithic device frame 160 that contains threads for attaching a threaded guide wire.

One Set of Struts

Figure 2A:
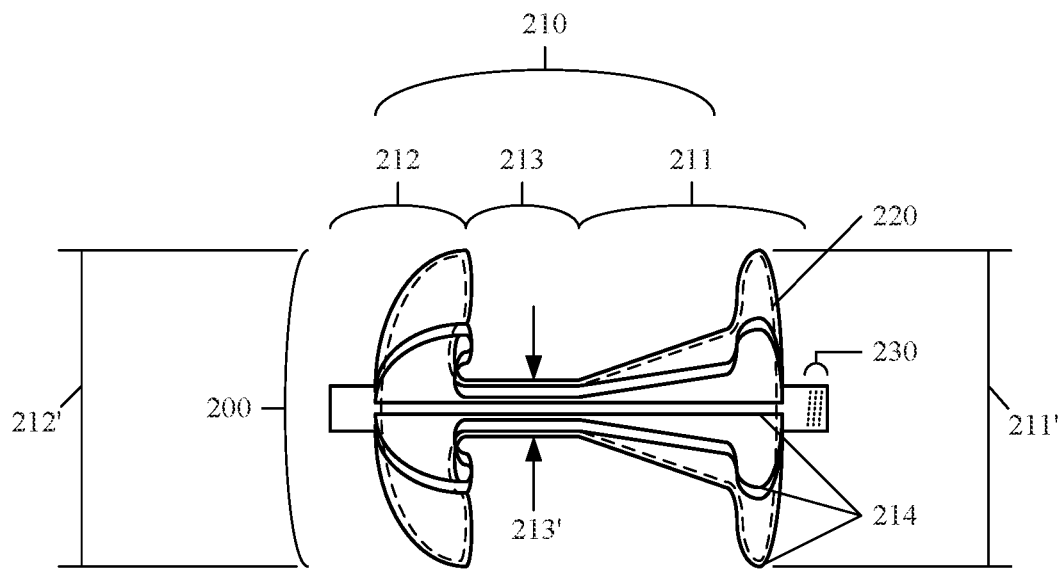
FIG. 2A is an exemplary diagram of a device having a single set of struts and a distally-tapered conical teardrop proximal structure, according to an embodiment.
Figure 2B:
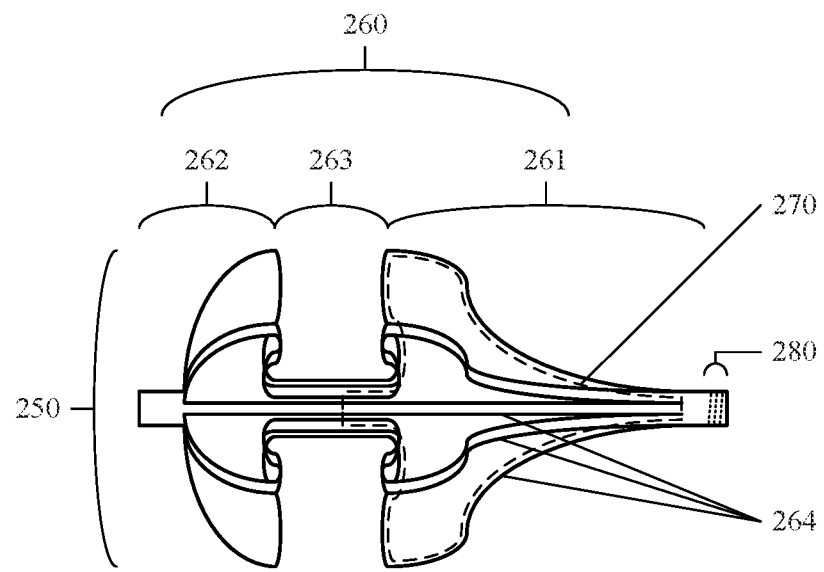
FIG. 2B is an exemplary diagram of a device having a single set of struts and a conical proximal structure, according to an embodiment.

In addition to a multiple strut set design, the device frame may be constructed from a single set of continuous struts running the length of the device frame. FIG. 2A and FIG. 2B are exemplary diagrams of devices having a single set of continuous struts, according to embodiments of the disclosure.

FIG. 2A is an exemplary diagram of a device 200 having a single set of struts and a distally-tapered conical teardrop proximal structure, according to embodiments of the disclosure. The device 200 includes a monolithic device frame 210, a shape memory polymer foam segment 220, and an attachment structure 230. The monolithic device frame 210 further includes a proximal structure 211, a distal structure 212, and an intermediate structure 213. The proximal structure 211, distal structure 212, and intermediate structure 213 are formed from the same set of struts 214. The proximal structure 211 has a distally-tapered (i.e., narrows as it moves distally) conical teardrop shape, the distal structure 212 has a concave disc shape, and the shape memory polymer foam segment 220 has a modified hourglass shape. The shape memory polymer foam segment 220 is coupled to the monolithic device frame 210 and contained within the proximal structure 211, distal structure 212, and intermediate structure 213. The attachment structure 230 is a segment on the monolithic device frame 210 that contains threads for attaching a threaded guide wire.

While FIG. 2A shows a concave face on distal portion 212 other embodiments may include a concave face on proximal portion 211 and some embodiments may include concave faces on portions 211 and 212.

FIG. 2B is an exemplary diagram of a device 250 having a single set of struts and a conical proximal structure, according to embodiments of the disclosure. The device 250 includes a monolithic device frame 260, a shape memory polymer foam segment 270, and an attachment structure 280. The monolithic device frame 260 further includes a proximal structure 261, a distal structure 262, and an intermediate structure 263. The proximal structure 261, distal structure 262, and intermediate structure 263 are formed from the same set of struts 264. The proximal structure 261 has a conical teardrop shape, the distal structure 262 has a concave disc shape, and the shape memory polymer foam segment 270 has a modified conical teardrop shape. The shape memory polymer foam segment 270 is coupled to the monolithic device frame 260 and contained within the proximal structure 261 and intermediate structure 263. The attachment structure 280 is a segment on the monolithic device frame 260 that contains threads for attaching a threaded guide wire.

While the concave face of portion 262 is on the proximal face of portion 262, in other embodiments a concave face may be on the distal face of portion 262. More generally, embodiments may include a concave face on a distal portion (on the distal and/or proximal faces of the distal portion) while other embodiments may include a concave face on a proximal portion (on the distal and/or proximal faces of the proximal portion) 211 and some embodiments may include concave faces on distal and proximal portions (on the distal and/or proximal faces of the distal and/or proximal portions).

Non-Monolithic Design

In embodiments of the disclosure, the device frame may be made from multiple, separate pieces (non-monolithic). For example, the proximal structure may formed from a first tube and the distal structure a second tube, with the proximal and distal structures joined together by an intermediate tube or wire.

Two Struts and Backbone Structure

Figure 3:
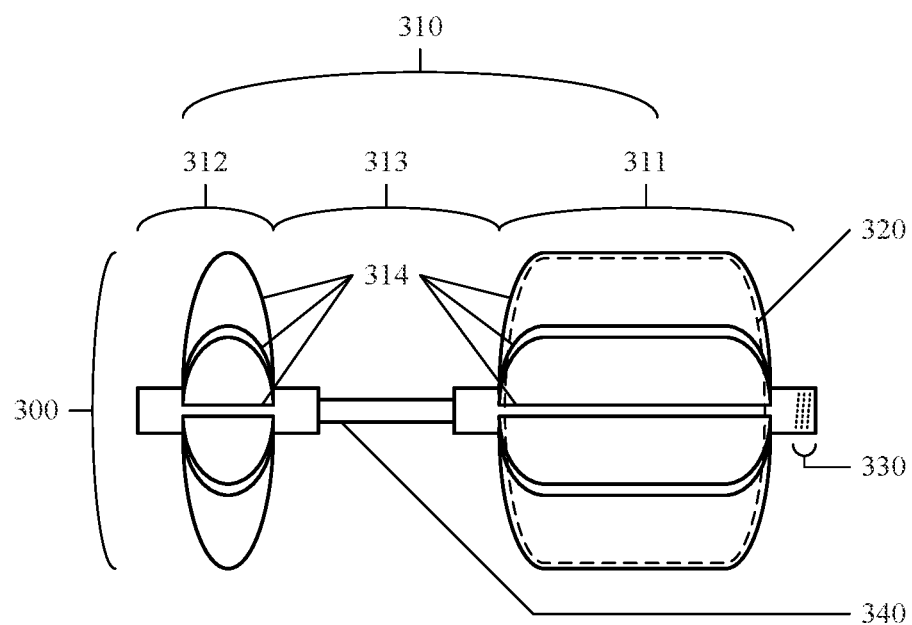
FIG. 3 is an exemplary diagram of a device having two sets of struts joined by a backbone structure, according to an embodiment.

In embodiments of the disclosure, the non-monolithic device frame may be formed from two sets of struts, each forming the proximal structure and the distal structure, coupled to a backbone, forming the intermediate structure. FIG. 3 is an exemplary diagram of a device 300 having two sets of struts joined by a backbone structure, according to embodiments of the disclosure. The device 300 includes a non-monolithic device frame 310, a shape memory polymer foam segment 320, an attachment structure 330, and a backbone structure 340. The non-monolithic device frame 310 further includes a proximal structure 311, a distal structure 312, and an intermediate structure 313. The proximal structure 311 and the distal structure 312 are formed from two separate sets of struts 314 coupled by an intermediate structure 313. The proximal structure 311 has a cylindrical shape, the distal structure 312 has a disc shape, and the shape memory polymer foam segment 320 has a cylindrical shape. The shape memory polymer foam segment 320 is coupled to the non-monolithic device frame 310 and contained within the proximal structure 311. The backbone structure 340 forms the intermediate structure 313 and couples the proximal structure 311 and the distal structure 312. The attachment structure 330 is a segment on the non-monolithic device frame 310 that contains threads for attaching a threaded guide wire.

Elastic Wires and End Structures

In embodiments of the disclosure, the non-monolithic device frame may be formed from a set of elastic wires attached to end support structures. These elastic wires may be preconfigured to a particular shape, wherein sections of each elastic wire may correspond to the proximal, distal, and intermediate structures once arranged and coupled to an end support structure. For example, a profile of the preconfigured shape of an elastic wire may have a first maxima corresponding to the proximal structure, a minima corresponding to the intermediate structure, and a second maxima corresponding to the distal structure. In some embodiments, the device may have 2-40 elastic wires for the device frame.

Figure 4:
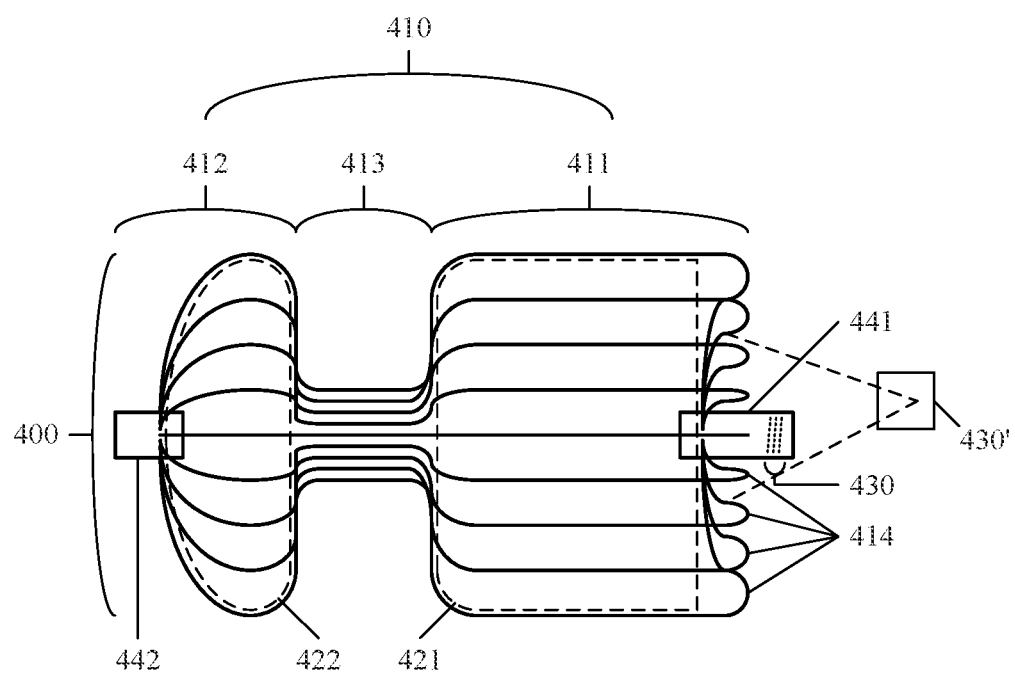
FIG. 4 is an exemplary diagram of a device having elastic wires and end support structures, according to an embodiment.

FIG. 4 is an exemplary diagram of a device 400 having elastic wires and end support structures, according to embodiments of the disclosure. The device 400 includes a non-monolithic device frame 410, a proximal shape memory polymer foam segment 421, a distal shape memory polymer foam segment 422, and an attachment structure 430. The non-monolithic device frame 410 further includes a proximal structure 411, a distal structure 412, and an intermediate structure 413. The proximal structure 411 further includes a proximal end structure 441 and the distal structure 412 further includes a distal end structure 442. The proximal structure 411 and distal structure 412 are formed from the same set of elastic wires 414. The elastic wires 414 are attached proximally to the proximal end structure 441 and distally to the distal end structure 442. The proximal structure 411 has a proximally concave cylindrical shape, the distal structure 412 has a proximally flat disc shape, the proximal shape memory polymer foam segment 421 has a cylindrical shape, and the distal shape memory polymer foam segment 422 has a proximally flat disc shape. The proximal shape memory polymer foam segment 421 is contained within and coupled to the proximal structure 411, and the distal shape memory polymer foam segment 422 is contained within and coupled to the distal structure 412. The attachment structure 430 is a segment on the proximal end structure 441 that contains threads for attaching a threaded guide wire.

Elastic Wire Braces and Backbone

In embodiments of the disclosure, the device frame may be formed from one or more sets of elastic wires coupled to a central backbone. These elastic wires may be arranged in a flower configuration to form petals that are configured to expand upon removal of an external restraint, such as the delivery tube. In some embodiments, the device may have 2-40 petals for each of the distal and proximal structures.

Figure 5A:
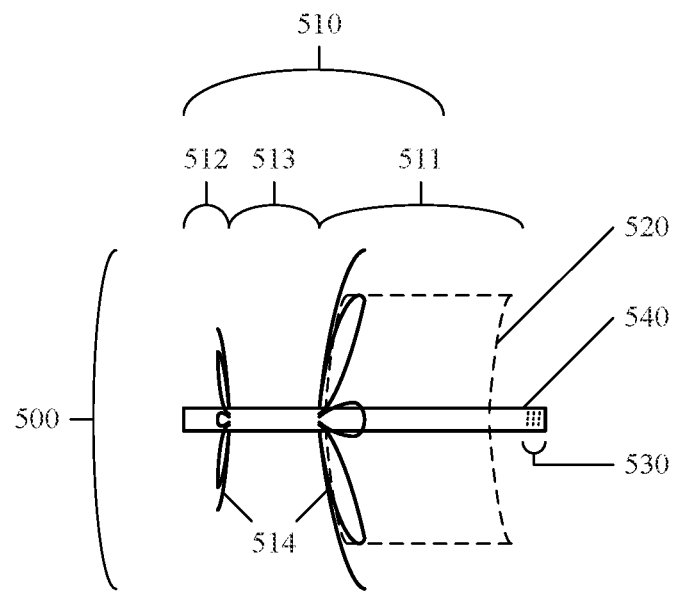
FIG. 5A is an exemplary diagram of a device having elastic wires in a flower configuration and a backbone structure, according to an embodiment.

FIG. 5A is an exemplary diagram of a device 500 having elastic wires in a flower configuration and a backbone structure, according to embodiments of the disclosure. The device 500 includes a non-monolithic device frame 510, a shape memory polymer foam segment 520, an attachment structure 530, and a backbone portion 540. The non-monolithic device frame 510 further includes a proximal structure 511, a distal structure 512, and an intermediate structure 513. The proximal structure 511 and the distal structure 512 are formed from two separate sets of elastic wires 514 which form flower configurations and coupled by the intermediate structure 513. The proximal structure 511 has a disc shape, the distal structure 512 has a disc shape, and the shape memory polymer foam segment 520 has a concave cylindrical shape. The shape memory polymer foam segment 520 is coupled to the backbone structure 540 proximal to the flower cage of the proximal structure 511. The backbone portion 540 forms the intermediate structure 513 of the non-monolithic device frame 510. The attachment structure 530 is a segment on the non-monolithic device 500 that contains threads for attaching a threaded guide wire.

Figure 5B:
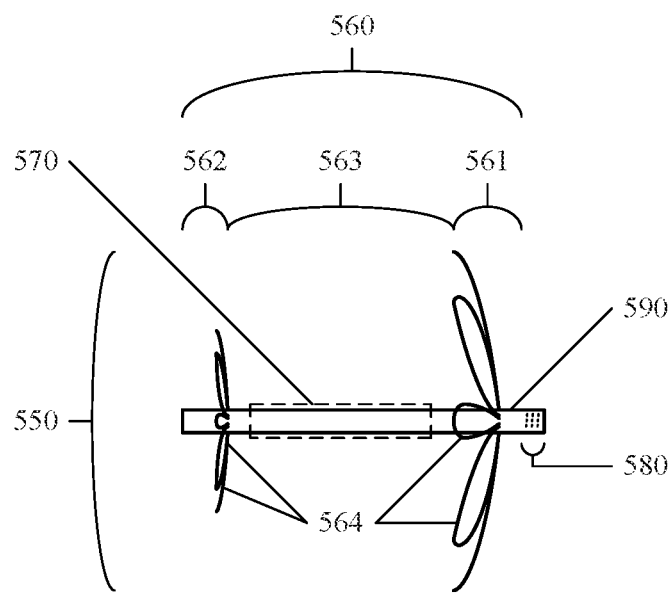
FIG. 5B is an exemplary diagram of a device having elastic wires in a flower configuration and a backbone structure, according to an embodiment.

FIG. 5B is an exemplary diagram of a device 550 having elastic wires in a flower configuration and a backbone structure, according to embodiments of the disclosure. The device 550 includes a non-monolithic device frame 560, a shape memory polymer foam segment 570, an attachment structure 580, and a backbone portion 590. The non-monolithic device frame 560 further includes a proximal structure 561, a distal structure 562, and an intermediate structure 563. The proximal structure 561 and the distal structure 562 are formed from two separate sets of elastic wires 564 which form flower configurations and coupled to the intermediate structure 563. The proximal structure 561 has a disc shape, the distal structure 562 has a disc shape, and the shape memory polymer foam segment 570 is in a compressed, non-actuated shape. The shape memory polymer foam segment 570 is coupled to the backbone portion 590 and contained within the intermediate structure 563. The backbone portion 590 forms the intermediate structure 563 of the non-monolithic device frame 560. The attachment structure 580 is a segment on the non-monolithic device 550 that contains threads for attaching a threaded guide wire.

Elastic Wire Cage and Backbone

Figure 6:
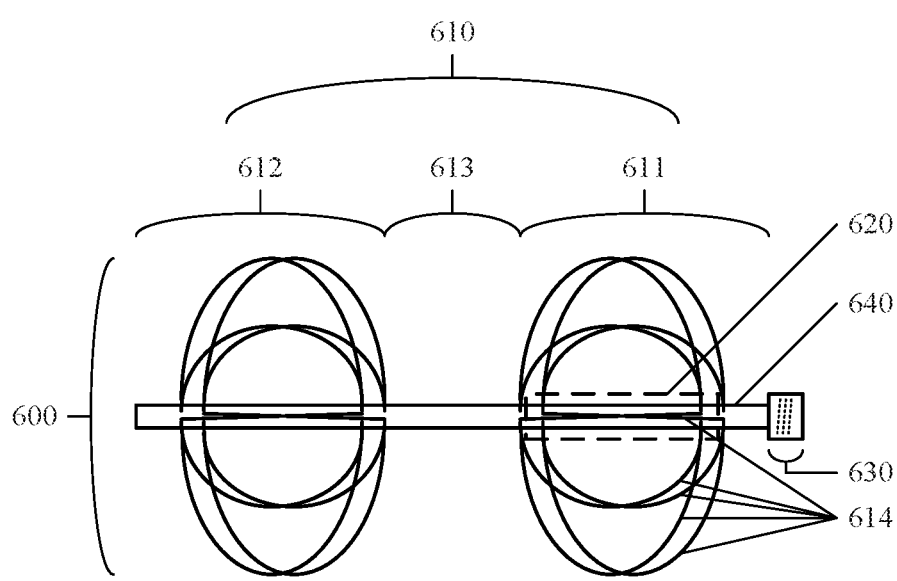
FIG. 6 is an exemplary diagram of a device having elastic wires in cage configurations and a backbone structure, according to an embodiment.

FIG. 6 is an exemplary diagram of a device 600 having elastic wires cage configurations and a backbone structure, according to embodiments of the disclosure. The device 600 includes a non-monolithic device frame 610, a shape memory polymer foam segment 620, an attachment structure 630, and a backbone structure 640. The non-monolithic device frame 610 further includes a proximal structure 611, a distal structure 612, and an intermediate structure 613. The proximal structure 611 and the distal structure 612 are formed from two separate sets of elastic wires 614 which form cage configurations and are coupled by the intermediate structure. The proximal structure 611 has a disc shape, the distal structure 612 has a disc shape, and the shape memory polymer foam segment 620 is in a compressed, non-actuated shape. The shape memory polymer foam segment 620 is coupled to the backbone portion 640 and contained within the proximal structure 611. The backbone portion 640 forms the intermediate structure 613 of the non-monolithic device frame 610. The attachment structure 630 is a separate segment attached to the non-monolithic device frame 610 that contains threads for attaching a threaded guide wire.

Proximal, Distal, and Intermediate Structures

The proximal structure may be configured to expand to a diameter greater than the proximal opening of the tissue channel to block the proximal structure from migrating through the proximal opening. The shape of the proximal structure may be configured based on selection criteria including, but not limited to, proximal opening shape, proximal cavity shape, flow characteristics, and foam shape. For example, the proximal opening of the tissue channel may be tapered out; in this case, a distally tapered plug-shaped proximal structure having an angle of 5-85 degrees from the central axis may be desired, to better fit to the proximal opening. As another example, the proximal structure may be configured to anticipate flex once deployed by including a concave distal surface to accommodate the flex and maintain a flat surface on the tissue wall around the proximal opening. The shape of the proximal structure may include, but is not limited to, discs, cylinders, concave cylinders, plugs, teardrops, cones, and tapered blocks.

The size of the proximal structure may be configured based on selection criteria including, but not limited to, proximal cavity size, proximal opening size, ratio of proximal structure diameter to proximal opening diameter, and shape memory polymer foam segment size. For example, in embodiments where the shape memory polymer foam is contained in the proximal structure, the proximal structure may be shaped to accommodate the foam segment while limiting movement. In some embodiments, the proximal structure may have a diameter of 2-60 mm and a length of 0.5-10 mm.

The distal structure may be configured to expand to a diameter greater than the distal opening of the channel to place the device during deployment and block the device from moving through the distal opening. For example, during device deployment, the distal structure may first exit the delivery device and expand into a distal cavity at the distal opening of the channel. The shape of the distal structure may be configured based on selection criteria including, but not limited to, distal opening shape, proximal cavity shape, flow characteristics, and shape memory polymer foam shape. The shape of the distal structure may include, but is not limited to, discs, concave discs, flat discs, cones, and tapered blocks.

The size of the distal structure may be configured based on selection criteria including, but not limited to, distal cavity size, distal opening size, ratio of distal structure diameter to distal opening diameter, and foam size. In some embodiments, the distal structure may have a diameter of 2-60 mm. and a length of 0.5-2 mm. For some applications having a proximal cavity at the proximal opening and/or a distal cavity at the distal opening, the proximal structure and/or distal structure may be configured to expand to contact one or more surfaces of the proximal cavity or distal cavity.

The intermediate structure may be positioned between the proximal structure and the distal structure and configured to fit in the channel after deployment. The size and shape of the intermediate structure may vary based on factors including, but not limited to, the diameter of the tissue channel, the length of the tissue channel, the shape memory polymer foam segment dimensions, and the design of the device frame. For example, for a device frame having continuous struts or elastic wires through the frame, the intermediate structure may be designed to have a diameter greater than the tissue channel diameter, but less than the proximal and distal structure diameters and capable of being fitted into the tissue channel. In some embodiments, the intermediate structure may have a length of 0.1-20 mm and a diameter 0.1-20 mm less than the lesser of the greatest proximal structure diameter and distal structure diameter.

The device frame may be constructed of elastic, biocompatible materials having a high strain recovery. In some embodiments, a shape memory alloy having a strain recovery of 3% may be used (however other embodiments are not so limited and may include shape memory elements with strain recovery of 4%, 6%, 8%, 10% or more). Materials that may be used include, but are not limited to: shape memory alloys; titanium alloys, such as nitinol; copper-base alloys, such as Cu—Al—Ni; platinum alloys, such as Fe—Pt; chromium-cobalt alloys, such as Co—Cr—Mo; cadmium-base alloys, such as Ag—Cd; shape memory polymers, such as urethane; and stainless steel. The device frame may be comprised of combinations of materials; for example, the proximal segment may be nitinol, the intermediate segment may be stainless steel, and the distal segment may be Co—Cr—Mo.

Backbone Structure

According to embodiments of the disclosure, a backbone structure may provide structure to the device frame and support the shape memory polymer foam segment. In some device designs, such as non-monolithic designs with non-continuous proximal and distal structures, the backbone structure may form the intermediate structure and connect the proximal and distal structures along the axis of the device. In other designs, the backbone structure may be part of the distal structure, proximal structure, or intermediate structure. The backbone structure may also secure or support the shape memory polymer foam segment. The shape memory polymer foam segment may be coupled to the backbone structure, such as through adhesion, compression, or foam formation on the backbone structure.

The backbone structure may be positioned along the central axis of the device for part or all of the device length. The backbone structure may be secured to the device at one or more points. For example, if the shape memory polymer foam segment is located in the proximal structure, the backbone may be located in the proximal structure and attached at the proximal end (e.g., element 441 of FIG. 4) to support contraction of the proximal structure length during deployment. For example and using FIG. 4 for illustrative purposes, in an embodiment a backbone (not present in FIG. 4 but is present in other versions of the embodiment of FIG. 4) is connected to the proximal cage stem 441 and the distal cage stem 442. Regardless of whether the struts are a SM alloy or other SM material (e.g., SMP), the backbone may be a SM material such as a SMP. The SMP backbone may be linear and have a non-actuated first length and a linear actuated second length (which is shorter than the first length). Thus, the SMP backbone would shorten or contract upon actuation while still providing support to expanding struts. With relatively larger devices this may help control torsion and other forces that may hinder deployment of the struts (i.e., may help the struts not tangle with each other). Factors that may influence where to position the backbone include, but are not limited to, shape memory polymer foam segment location, frame type, and frame expansion and contraction properties.

The backbone structure may be comprised of any biocompatible material capable of supporting the shape memory polymer foam segment or connecting of the proximal and distal structures. Materials that may be used include, but are not limited to: shape memory alloys; titanium alloys, such as nitinol; copper-base alloys, such as Cu—Al—Ni; platinum alloys, such as Fe—Pt; chromium-cobalt alloys, such as Co—Cr—Mo; cadmium-base alloys, such as Ag—Cd; shape memory polymers, such as urethane; and stainless steel. The backbone structure may be solid, such as a wire or rod, or may be open, such as a tube or mesh. Factors that may influence backbone structure material selection include, but are not limited to, tensile strength for structure connection, surface roughness for shape memory polymer adhesion, biocompatibility, and biodegradability.

Shape Memory Polymer Foam Segment

According to embodiments of the disclosure, the device may contain a shape memory polymer foam segment. The shape memory polymer foam segment may be used to compress into a delivery tube, actuate and expand upon deployment, and occlude flow through the channel. For certain applications, the shape memory polymer may also promote healing, tissue migration, or clotting. The shape memory polymer foam segment may be coupled to the device, including the device frame and a backbone structure. The shape memory polymer foam segment may be positioned at various locations on or in the device frame including, but not limited to, the proximal structure, the distal structure, the intermediate structure, or combinations of the aforementioned structures.

According to embodiments of the disclosure, the shape memory polymer foam segment may be comprised of any shape memory foam capable of compressing into a delivery tube as a temporary shape, actuating from an external stimulus after delivery, and expanding to block a channel as a permanent shape. Shape memory polymers that may be used include, but are not limited to: thermally-induced shape memory polymers, such as thermoset or thermoplastic shape memory polymers that include polyurethanes, polyethylene terephthalate (PET), and polyethylene oxide (PEO); photon-induced shape memory polymers, such as shape memory polymers with cinnamamide moieties; laser-actuated shape memory polymers; chemically-actuated shape memory polymers; and electrically-actuated shape memory polymers, such as carbon nanotube-filled shape memory polymers.

Shape memory polymers may be tailored to or selected for properties that may include, but are not limited to: transition temperatures, foam density, shape recovery, type and mechanism of actuation, biodegradability, volume recovery, cell structure, cell interconnectedness, porosity, and surface adhesion. Types of actuation may include, but are not limited to, heat, light, laser, and chemical. For example, in some embodiments, the shape memory polymer foam segment may actuate on contact with a bodily fluid, such as blood. As another example, for applications in which tissue migration or scaffolding may be desired, the shape memory polymer may be biodegradable. As another example, for applications involving partial flow, such as blood clotting, the shape memory polymer foam may have an open cell structure; for applications involving no fluid flow, the shape memory polymer foam may have a closed cell structure. In certain embodiments, the shape memory polymer foam may be configured to a high volume recovery in a range of 50-100.

In addition to the shape memory polymer foam, additives may be included in the shape memory polymer foam segment. Some additives may be included to assist in the occlusion function of the device. For example, if the device is to be used to occlude a channel for blood flow, a coagulant may be included. In another example, if the foam or device frame is chemically actuated, a chemical may be included. Additives may also be added to provide an additional functionality to the device. For example, if healing or tissue migration is desired, a medication may be included to assist in either of these functions. Additives that may be used include, but are not limited to, coagulants, medications, structure components, actuation agents, and particulate fillers to improve image contrast or mechanical properties.

The shape memory polymer foam segment may have a variety of shapes, sizes, and configurations for its permanent and temporary states. Factors that may influence shape and size selection may include, but are not limited to, device frame shape, proximal structure shape, distal structure shape, intermediate structure shape, channel shape, channel opening configuration, delivery tube inner diameter. Shapes that may be used include, but are not limited to, plug, cylinder, concave cylinder, hourglass, cone, and tapered block.

Attachment Structure

According to embodiments of the disclosure, the device may include an attachment structure for attaching and detaching the device from a deployment mechanism. The attachment structure may be integrated into another part of the device or may be a separate structure. For example, in a monolithic device having a single tube, the end of the tube may have threads for receiving a threaded guide wire. In a device having a backbone, a separate attachment structure may be coupled to the device. Mechanisms used for the attachment structure may include, but are not limited to, threads, notches-and-release, hooks, and magnets.

Manufacture of Monolithic Proximal and Distal Structures

Methods for manufacturing devices having monolithic proximal and distal structures may include creating struts for a device frame, shape setting the struts, coupling the shape memory polymer foam segment to the device, and configuring the device with an attachment structure.

Figure 7:
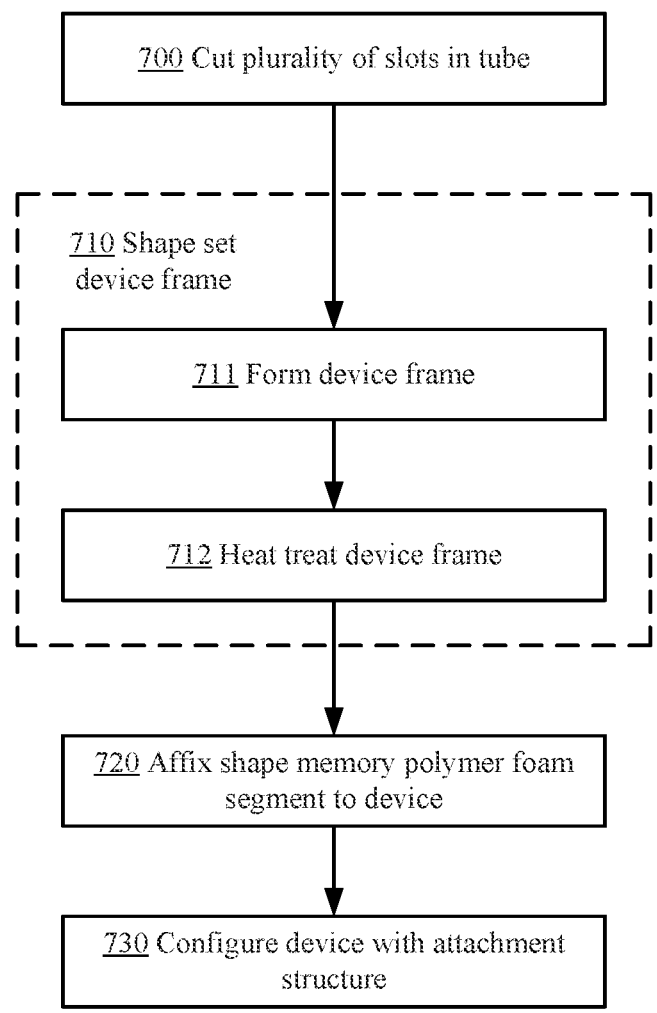
FIG. 7 is an exemplary flow chart for manufacturing an elastic metal device, according to an embodiment.

FIG. 7 is an exemplary flow chart for manufacturing an elastic metal device, according to embodiments of the disclosure. A plurality of slots is cut into an elastic tube, as in 700. Cutting slots in a tube, wire, or rod may create the form of struts used for later formation of the proximal, distal, and/or intermediate structures. For devices having continuous struts down the device frame, a single set of slots may be cut; for devices have separate struts for the proximal and distal structures, two or more sets of slots may be cut subsequently or concurrently. The struts may be cut by a laser or other precision cutting device.

The device frame may be shape set, as in 710. Shape setting may involve creating a permanent shape for the device frame. For metal frames, shape setting may include molding the device frame to an expanded shape to which the device returns when radial restrictions are removed, such as through deployment from a tube. The device frame shape set of 710 may include forming a device frame, as in 711, and heat treating the device frame, as in 712.

Device formation 711 may be performed by setting the tube in a mold structure and compressing the tube so that the struts expand into a preconfigured shape. Spacers corresponding to desired structure length may be placed in the corresponding section of tube; for example, a 10 mm spacer may be placed in a section of tube corresponding to the proximal structure, where the desired proximal structure length is 10 mm. An external frame tailored to the desired structure diameter may be placed around the corresponding section of tube. The tube may be compressed axially until the lateral struts contact the external frame and/or the internal radial struts contact the spacer. The process may be applied subsequently or concurrently to other sections of the device frame. After formation of the preconfigured shape, the device may be heat treated to create a permanent shape to which the device frame will return to once external restrictions are removed. A backbone structure may be coupled to the device along the device axis, such as through welding, adhesion, or tension.

A shape memory polymer foam segment may be coupled to the device, as in 720. The shape memory polymer foam segment may be coupled to the device frame by mechanisms that include, but are not limited to: adhering the shape memory polymer foam segment to the device frame through application of an adhesive to a portion of the device frame; crimping the device frame to the shape memory polymer foam segment; or pressing the shape memory polymer foam segment into the frame through foam pressure. The shape memory polymer foam segment may be coupled to a backbone structure by mechanisms that include, but are not limited to: adhering the shape memory polymer foam segment to the backbone structure through application of an adhesive to a portion of the backbone structure; compressing the shape memory polymer foam segment to the backbone structure; or forming the shape memory polymer foam segment directly onto the backbone structure.

The device may be configured with an attachment structure, as in 730. Configuring the device with an attachment structure may include modifying the device to include an attachment and detachment mechanism. For example, if the device tube is formed from a tube, the inside of the tube at the proximal end of the device may be threaded so that a guide wire may be screwed into and unscrewed from the device. Configuring the device with an attachment structure may also include coupling a separate structure having an attachment and detachment mechanism to the device. For example, the screw action discussed above may be attached to the proximal end of the device to accommodate a different size of guide wire.

Figure 8:
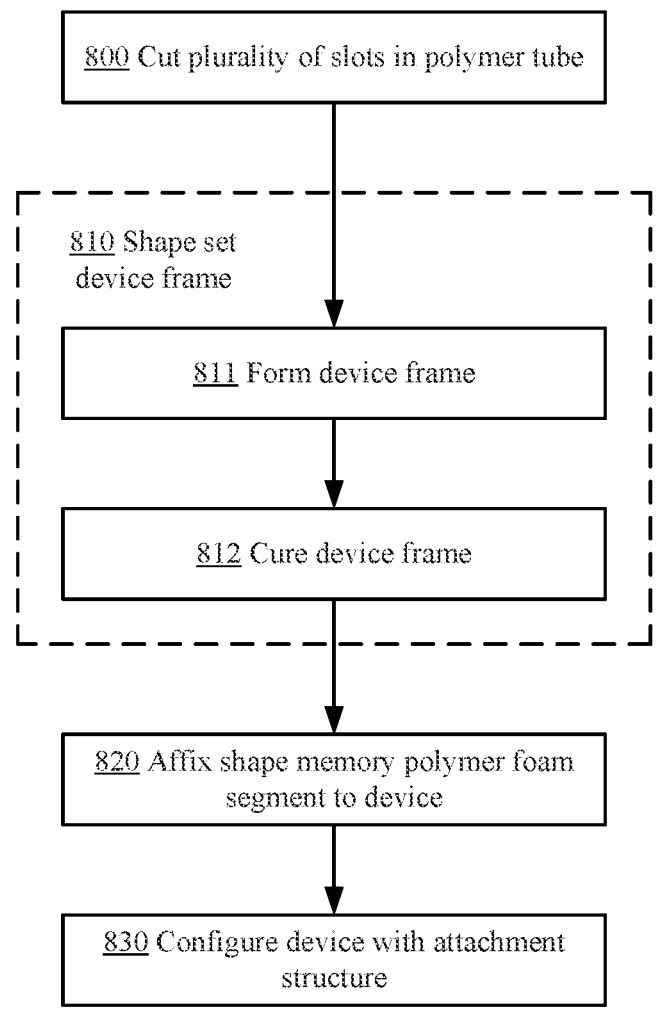
FIG. 8 is an exemplary flow chart for manufacturing a shape memory polymer device, according to an embodiment.

FIG. 8 is an exemplary flow chart for manufacturing a shape memory polymer device, according to embodiments of the disclosure. A plurality of slots may be cut into a shape memory polymer tube, as in 800. The device frame may be shape set, as in 810. The device frame shape set of 810 may include forming a device frame, as in 811, and curing the device frame, as in 812. Forming the device frame may include molding struts to a preconfigured shape. Alternatively, a shape memory polymer frame may be created from injection molding.

Curing the device frame may include crosslinking the polymer to create a rigid frame in the preconfigured shape. A shape memory polymer foam segment may be coupled to the device, as in 820, including those methods discussed in

720 of FIG. 7. The device may be configured with an attachment structure, as in 830, including those methods discussed in 730 of FIG. 7.

In some embodiments, separate tubes may be used to create monolithic proximal and distal structures, as in FIG. 3. The proximal and distal structures may be coupled with an intermediate structure, such as a backbone structure. Methods that may be used include, but are not limited to, welding, adhesion, or tension.

Manufacture of Non-Monolithic Proximal and Distal Structures

Manufacture of devices having non-monolithic proximal and distal structures may include providing elastic wires for a device frame, coupling the elastic wires to an axial support structure, coupling the shape memory polymer foam segment to the device, and configuring the device with an attachment structure.

Figure 9:
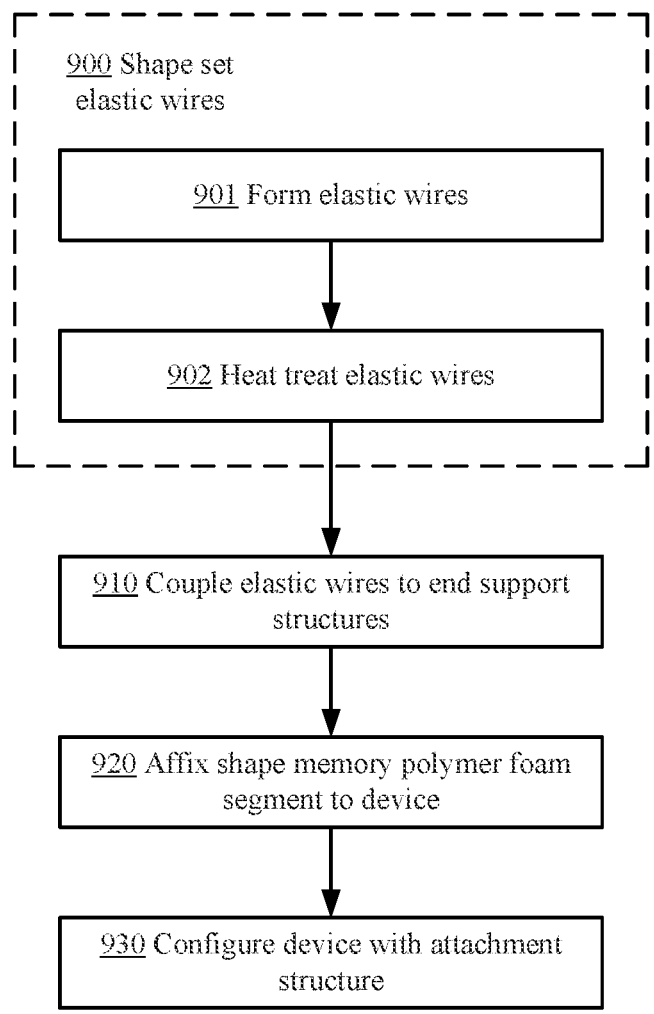
FIG. 9 is an exemplary flow chart for manufacturing a non-monolithic device having elastic wires and end structures, according to an embodiment.

FIG. 9 is an exemplary flow chart for manufacturing a non-monolithic device having elastic wires and end structures, according to embodiments of the disclosure. Elastic wires are shape set, as in 900. The elastic wire shape set of 900 may include forming the elastic wires, as in 901, and heat treating the elastic wires, as in 902. Alternatively, in shape memory polymer frame designs, elastic wire shape setting may include injection molding the elastic wires and curing the wires. The elastic wires are coupled to end structures, as in 910. This may be performed by welding, soldering, adhesion, screwing, or tension. Holes may be drilled in the end structures to accommodate the elastic wires. A shape memory polymer foam segment may be coupled to the device, as in 920, including those methods discussed in 720. The device is configured with an attachment structure, as in 930, including those methods discussed in 730.

Figure 10:
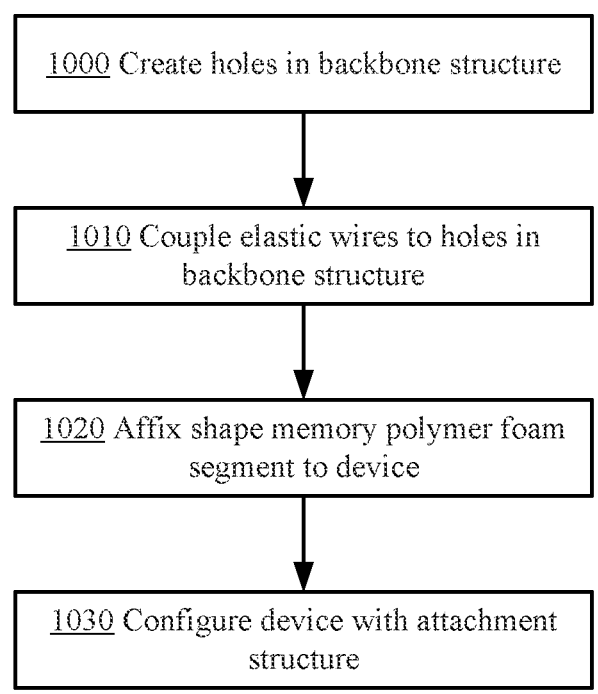
FIG. 10 is an exemplary flow chart for manufacturing a non-monolithic device having elastic wires and a backbone structure, according to an embodiment.

FIG. 10 is an exemplary flow chart for manufacturing a non-monolithic device having elastic wires and a backbone structure, according to embodiments of the disclosure. Holes may be created in a backbone structure, as in 1000. Elastic wires may be coupled to the holes created in 1000, as in 1010. A shape memory polymer foam segment may be coupled to the device, as in 1020, including those methods discussed in 720. The device may be configured with an attachment structure, as in 1030, including those methods discussed in 730.

The following examples pertain to further embodiments.

Example 1. A device for a tissue channel having a proximal opening and a distal opening, comprising: a device frame having a central axis and comprising: a proximal structure configured to: collapse to fit into a delivery structure; expand to block migration of the proximal structure through the proximal opening; a distal structure configured to: collapse to fit into the delivery structure; expand to block migration of the distal structure through the distal opening; an intermediate structure coupled to the proximal structure and the distal structure and configured to fit in the tissue channel upon device deployment; a shape memory polymer foam segment coupled to the device frame and configured to: compress to fit into the delivery structure; expand to occlude flow through the channel; and an attachment structure coupled to the device frame and configured to attach and detach the device from a delivery guide.

Example 2. The device of example 1, further comprising a backbone structure coupled to the device frame and located approximately along the central axis of the device frame.

Example 3. The device of example 2, wherein the backbone structure is an elastic, biocompatible material.

Example 4. The device of example 3, wherein the backbone structure is comprised of a titanium alloy, a platinum alloy, a chromium-cobalt alloy, a shape memory polymer, or stainless steel.

Example 5. The device of example 1, wherein: the shape memory polymer foam segment is further configured to expand radially to a cross sectional area greater than an area of the proximal opening; the proximal structure is further configured to expand radially to a diameter greater than a diameter of the proximal opening; and the distal structure is further configured to expand radially to a diameter greater than a diameter of the distal opening.

Example 6. The device of example 1, wherein the shape memory polymer foam segment has a volume recovery in a range of 50-100.

Example 7. The device of example 1, wherein at least a portion of the shape memory polymer foam segment is open cell.

Example 8. The device of example 1, wherein the shape memory polymer foam segment contains a filler.

Example 9. The device of example 8, wherein the filler comprises a hydrogel, a blood additive, a coagulant, a medication, or a particulate filler to improve image contrast or mechanical properties.

Example 10. The device of example 1, wherein the shape memory polymer foam segment is actuated with laser irradiation, a solvent, or body heat.

Example 11. The device of example 1, wherein the shape memory polymer foam segment is configured to expand to a cylindrical, conical, hourglass, or diamond form.

Example 12. The device of example 1, wherein the shape memory polymer foam segment is 1-30 mm in diameter.

In another version of Example 12 the device of example 1, wherein the shape memory polymer foam segment is 1-60 mm in diameter.

Example 13. The device of example 1, wherein the shape memory polymer foam segment is comprised of a proximal segment in the proximal structure and a distal segment in the distal structure.

Example 14. The device of example 1, wherein the shape memory polymer foam segment is secured within the device frame through adhesion to the device frame, crimping the device frame to the foam, or outward foam pressure on the device frame.

Example 15. The device of example 2, wherein the shape memory polymer foam segment is secured to the backbone portion by adhesion to the backbone structure or foam compression on to the backbone portion, or foam formation directly over the backbone portion.

Example 16. The device of example 5, wherein: the proximal structure is configured to: expand to a diameter greater than a diameter of the proximal opening by a factor of 2-5; compress to a diameter less than an inner diameter of the delivery structure; the distal structure is configured to: expand to a diameter greater than a diameter of the distal opening by a factor of 1.5-5; and compress to a diameter less than the inner diameter of the delivery structure.

Example 17. The device of example 1, wherein the proximal structure and the distal structure are each comprised of an elastic frame of struts.

Example 18. The device of example 1, wherein the device frame is comprised of an elastic biocompatible metal configured to recover from deformations.

Example 19. The device of example 18, wherein the elastic biocompatible metal is a shape memory alloy.

Example 20. The device of example 18, wherein the device frame is comprised of a titanium alloy, a platinum alloy, a chromium-cobalt alloy, a copper-aluminum alloy, or stainless steel.

Example 21. The device of example 1, wherein: the proximal structure has a diameter of 2-40 mm and a length of 0.5-10 mm; and the distal structure has a diameter of 2-40 mm and a length of 0.5-2 mm.

Example 22. The device of example 1, wherein the device frame is a monolithic shape memory polymer frame comprised of a shape memory polymer.

Example 23. The device of example 22, wherein at least a portion of the shape memory polymer frame contains a laser-absorbing dye.

Example 24. The device of example 23, wherein the shape memory polymer frame is configured for actuation by laser irradiation, a solvent, or body heat.

Example 25. The device of example 22, wherein the shape memory polymer frame is biodegradable.

Example 26. The device of example 22, wherein the shape memory polymer frame is configured to undergo plasticization from contact with a solvent from the delivery structure.

Example 27. The device of example 1, wherein the proximal structure is in the form of a cylinder, concave cylinder, tapered cylinder, cone, plug, or disc.

Example 28. The device of example 1, wherein the distal structure is in the form of a cone, flat disc, or concave disc.

Example 29. The device of example 1, wherein a proximal end of the proximal structure is 1-5 mm greater than a distal end of the proximal structure.

Example 30. The device of example 1, wherein the proximal structure is in a conical form with a tapered surface at a proximal end of the proximal structure and wherein the tapered surface forms a 5-85 degree angle relative to the central axis of the device frame.

Example 31. The device of example 1, wherein the proximal structure is in a form of a cylinder with a concave surface at a proximal end of the proximal structure and wherein the concave surface forms a 5-85 degree angle relative to the central axis of the device frame.

Example 32. The device of example 1, wherein the distal structure is in a form of a concave disc with a concave surface at a distal end of the distal structure and wherein the concave surface has a 5-85 degree angle relative to the central axis of the device frame.

Example 33. The device of example 14, wherein the proximal structure and the distal structure are each comprised of 2-30 struts.

Example 34. The device of example 33, wherein the struts are straight or helixed.

Example 35. The device of example 33, wherein the proximal structure, intermediate structure, and distal structure are comprised of continuous struts.

Example 36. The device of example 33, wherein the proximal structure is comprised of a first set of struts and the distal structure is comprised of a second set of struts.

Example 37. The device of example 2, wherein the proximal structure and the distal structure are comprised of one or more sets of elastic wires in flower configurations and are connected to the backbone structure.

Example 38. The device of example 33, wherein: each flower configuration is comprised of 2-60 petals; and the proximal structure and the distal structure are each 4-40 mm in diameter.

Example 39. The device of example 37, wherein the proximal structure and the distal structure each have two or more interwoven sets of elastic wires.

Example 40. The device of example 37, wherein the sets of elastic wires are attached approximately perpendicular to the axis of the device frame.

Example 41. The device of example 37, wherein the flowers are curved proximally or distally.

Example 42. The device of example 1, wherein the device contains a radiopaque marker on at least one of the proximal structure, distal structure, or intermediate structure.

Example 43. The device of example 2, wherein the proximal, distal, and intermediate structures are comprised of a plurality of elastic wires coupled to the backbone structure at a proximal end and a distal end of the device.

Example 44. The device of example 43, wherein the proximal, distal, intermediate structures are comprised of 2-50 elastic wires.

Example 45. The device of example 1 wherein the proximal and distal structures are formed from two different elastic materials.

Example 46. The device of example 1, wherein the intermediate structure has a diameter less than 1-10 mm of the lesser of a diameter of the proximal structure or a diameter of the distal structure.

Example 47. The device of example 1, wherein the intermediate structure has a length of 0.1-20 mm.

Example 48. The device of example 18, wherein the intermediate structure is configured to shorten axially when actuated.

Example 49. The device of example 1, wherein the device is monolithic and the intermediate structure forms a depression in a profile of the device frame.

Example 50. The device of example 1, wherein the attachment structure is threaded.

Example 51. The device of example 1, wherein: the tissue channel couples a proximal vascular cavity and a distal vascular cavity; and the proximal structure is configured to contact at least a surface of the proximal vascular cavity.

Example 52. The device of example 51, wherein the tissue channel is a patent ductus arteriosus.

Example 53. The device of example 51, wherein the tissue channel is a patent foramen ovale.

Example 54. The device of example 51, wherein the tissue channel is a ventricular septal defect.

Example 55. A method for creating a device for a tissue channel, comprising: creating a plurality of slots in one or more elastic tubes; shape setting the one or more elastic tubes to a preconfigured shape to form a device frame having a proximal structure, a distal structure, and an intermediate structure, wherein the proximal structure and distal structure each have a larger diameter than the intermediate structure; configuring an attachment structure to the device frame; and coupling a shape memory polymer foam segment to the device frame.

Example 56. The method of example 55, wherein: the plurality of slots are continuous through the proximal structure, distal structure, and intermediate structure; and the device frame is comprised of a single elastic tube.

Example 57. The method of example 55, wherein: the device frame is comprised of a single elastic tube; creating a plurality of slots further comprises: creating a first plurality of slots in a first section of the single elastic tube; creating a second plurality of slots in a second section of the single elastic tube; shape setting the elastic tube to a preconfigured shape further comprises: shape setting the first section of the single elastic tube to form the proximal structure; shape setting the second section of the single elastic tube to form the distal structure.

Example 58. The method of example 55, wherein: creating a plurality of slots further comprises: creating a first plurality of slots in a first section of a first elastic tube; creating a second plurality of slots in a second section of a second elastic tube; shape setting the elastic tube to a preconfigured shape further comprises: shape setting the first section of the first elastic tube to form the proximal structure; shape setting the second section of the second elastic tube to form the distal structure; and coupling the proximal structure and the distal structure with the intermediate structure.

Example 59. The method of example 55, further comprising coupling a support structure to a distal end of the device frame.

Example 60. The method of example 55, further comprising coupling a backbone structure to the device frame.

Example 61. The method of example 55, wherein coupling the shape memory polymer foam segment further comprises adhering the shape memory polymer foam segment to the device frame with an adhesive.

Example 62. The method of example 55, wherein coupling the shape memory polymer foam segment further comprises crimping the device frame to the shape memory polymer foam segment.

Example 63. The method of example 60, wherein coupling the shape memory polymer foam segment further comprises adhering the shape memory polymer foam segment to the backbone structure.

Example 64. The method of example 60, wherein coupling the shape memory polymer foam segment further comprises compressing the foam to the backbone structure.

Example 65. The method of example 60, wherein coupling the shape memory polymer foam segment further comprises depositing the shape memory polymer foam segment on the backbone during foam formation.

Example 66. The method of example 55, wherein: the elastic tube is comprised of a thermoplastic shape memory polymer; shape setting the one or more elastic tubes further comprises curing the thermoplastic shape memory polymer.

Example 67. A method for creating a device for a tissue channel, comprising: creating an elastic device frame through one of injection molding, additive manufacturing, or subtractive manufacturing, wherein the device frame has a proximal structure, a distal structure, and an intermediate structure, and wherein the proximal structure and distal structure each have a larger diameter than the intermediate structure; configuring an attachment structure to the device frame; and coupling a shape memory polymer foam segment to the device.

Example 68. The method of example 68 wherein: the elastic device frame is comprised of a thermoplastic shape memory polymer; and creating the elastic device further comprises curing the thermoplastic shape memory polymer.

Example 69. The method of example 68, wherein curing the thermoplastic shape memory polymer further comprises cross-linking the thermoplastic shape memory polymer.

Example 70. A method for creating a device for a tissue channel, comprising: coupling a plurality of elastic wires to one or more axis support structures to form a device frame with a preconfigured shape having a proximal structure, a distal structure, and an intermediate structure, wherein the proximal structure and the distal structure each have a diameter greater than a diameter of the intermediate structure; configuring an attachment structure to the device frame; and coupling a shape memory polymer foam segment to the device.

Example 71. The method of example 70: wherein the one or more axis support structures further comprise: a proximal end structure; a distal end structure; wherein each elastic wire in the plurality of elastic wires has a proximal end and a distal end; further comprising: shape setting each elastic wire in the plurality of elastic wires to a preconfigured shape; wherein coupling the plurality of elastic wires further comprises: coupling the proximal end of each elastic wire in the plurality of elastic wires to the proximal end structure; and coupling the distal end of each elastic wire in the plurality of elastic wires to the distal end structure.

Example 72. A method for creating a device having a proximal section and a distal section, comprising: creating a first plurality of holes into a first section of a backbone structure which corresponds to the proximal section of the device; creating a second plurality of holes into a second section of the backbone structure which corresponds to the distal section of the device; and affixing elastic wires through the first plurality of holes to form a proximal flower structure and the second plurality of holes to form a distal flower structure; affixing the attachment structure to the proximal end of the device; and affixing a compressed shape memory polymer foam to the device.

Example 73. The method of example 72, further comprising shape setting the proximal and distal flower structures.

Example 74. A method for creating a device having a proximal section, an intermediate section, and a distal section, comprising: providing a plurality of elastic wires, wherein each elastic wire has a proximal end and a distal end; shape setting each elastic wire to a preconfigured shape, wherein the preconfigured shape has a first maxima section, a minima section, and a second maxima section; securing the proximal ends of the elastic wires to a proximal end structure and the distal ends of the elastic wires to a distal end structure to form a device frame having a proximal structure from at least a portion of the first maxima section of each elastic wire, a distal structure from at least a portion of the second maxima section of each elastic wire, and an intermediate structure from at least a portion of the minima section of each elastic wire; affixing an attachment structure to the device frame; and affixing a compressed shape memory polymer foam segment to the device.

Example 75. A method for creating a device having a proximal section and a distal section, comprising: creating a first plurality of slots into a first elastic tube which corresponds to the proximal section of the device; creating a second plurality of slots into a second elastic tube which corresponds to the distal section of the device; and shape setting the first elastic tube to form a proximal structure and the second elastic tube to form a distal structure; connecting the first elastic tube and the second elastic tube with an intermediate section to form a device frame; configuring an attachment structure to the device frame; coupling a compressed shape memory polymer foam to the device.

Example 1a. A system comprising: a conduit comprising: (a)(i) a proximal portion including proximal struts, (a)(ii) a distal portion including distal struts, and (a)(iii) a middle portion coupling the proximal struts to the distal struts; and a shape memory polymer (SMP) foam that expands from an unactuated configuration to an actuated configuration; wherein (b)(i) the proximal and distal struts include a shape memory (SM) material, (b)(ii) the proximal struts expand from a first proximal configuration to a second proximal configuration and the distal struts expand from a first distal configuration to a second distal configuration, (b)(iii) the second proximal configuration has a larger maximum outer diameter than the first proximal configuration and the second distal configuration has a larger maximum outer diameter than the first distal configuration, and (b)(iv) the SMP foam is, in the unactuated configuration, included within the proximal struts when the proximal struts are in the second proximal configuration.

The SMP foam may actuate based on, for example, being heated beyond its Tg. The heat may be due to blood temperature, optics, electrical resistive heating, and the like. For example, FIGS. 3 and 4 depict proximal and distal struts in the "second proximal configuration" and "second distal configuration". The "first proximal configuration" and "first distal configuration" may exist when the device is contained within a deployment conduit, such as a sheath or catheter. The struts "expand" in that they, for example, assume a larger outer diameter once deployed from a sheath (where the diameter is measured radially and orthogonally to the central axis of the device). The proximal and distal struts may be monolithic with each other (e.g., FIG. 4) or not (e.g., FIG. 3). The middle portion may include struts (e.g., FIG. 4) or may not include struts (e.g., FIG. 3). Regarding the SMP foam being included within the proximal struts, FIGS. 1A and 2A both show such a situation.

Figure 13A:
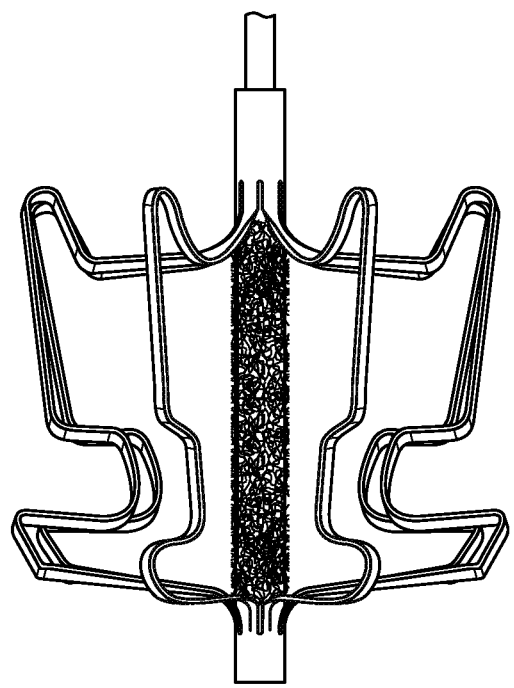
FIG. 13A and FIG. 13B respectively depict an embodiment with expanded struts and an unactuated foam and an embodiment with expanded struts and an actuated foam.
Figure 13B:
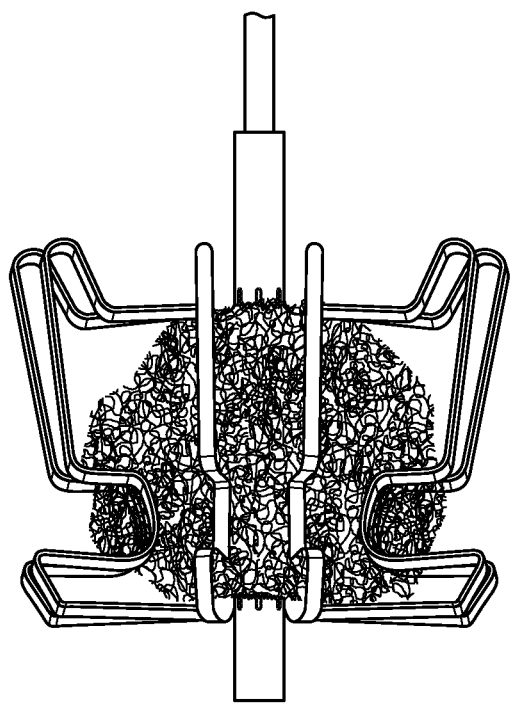

As another example, see FIGS. 13A and 13B. FIG. 13A shows an embodiment with the struts in the second proximal and second distal configurations (i.e., expanded) but with the foam in an unactuated state. FIG. 13B shows an embodiment with the struts in the second proximal and second distal configurations but with the foam in an actuated state. FIG. 13A may depict the device at a manufacturing facility before the device is included in a sheath and packaged for shipping to customers.

Example 2a. The system of example 1a, wherein the proximal, middle, and distal portions are all part of the conduit and are all monolithic with each other.

For example, the three portions may be cut from a conduit and or extruded in such a fashion they all form the conduit and are monolithic (i.e., formed from a single unit and not coupled via welding, adhesives, and the like).

Example 3a. The system of example 2a wherein the middle portion includes no struts.

For example, see FIG. 1A. This is not to say the distal and proximal struts are not, for example, cut from a single conduit. FIG. 1A merely shows a contiguous ring (that includes no struts) in area 113.

Example 4a. The system of example 1a, wherein the SMP foam is monolithic and the SMP foam is, in the unactuated configuration, included within the middle portion.

For example, see FIG. 2A (albeit this shows the actuated configuration).

Example 5a. The system of example 4a, wherein the SMP foam is, in the unactuated configuration, included within the distal struts when the distal struts are in the second distal configuration.

For example, see FIG. 2A (albeit this shows the actuated configuration). For example, see FIG. 13A.

Example 6a. The system of example 4a, wherein the SMP foam, in both the unactuated and actuated configurations, is included within the proximal struts when the proximal struts are in the second proximal configuration, the middle portion, and the distal struts when the distal struts are in the second distal configuration.

For example, see FIG. 2A. See also, for example, FIG. 12 (C.3). See also FIGS. 13A and 13B. When the device of FIG. 13A is included in a sheath or catheter, the distal struts may be deformed forward whereby the unactuated foam may no longer be included within the distal struts. Even in such a deformed state within a sheath, the unactuated foam may still be within the proximal struts.

Example 7a. The system of example 4a, wherein each of the proximal struts are generally collinear, respectively, with each of the distal struts when the proximal and distal struts are respectively in the second proximal and second distal configurations.

For example, see FIG. 1A or 2B.

Example 8a. The system of example 4a wherein each of the second proximal configuration and second distal configuration has a larger outer diameter than a maximum diameter of the middle portion.

For example, the embodiments of FIGS. 1A, 1B, 2A, 2B include a narrowed waist. A "maximum" outer diameter of, for example, FIG. 2A for each of portions 212, 213, 211 are respectfully diameters 212', 213', 211'.

Example 9a. The system of example 8a wherein the second proximal configuration has a smaller maximum outer diameter than the second distal configuration.

Figure 12:
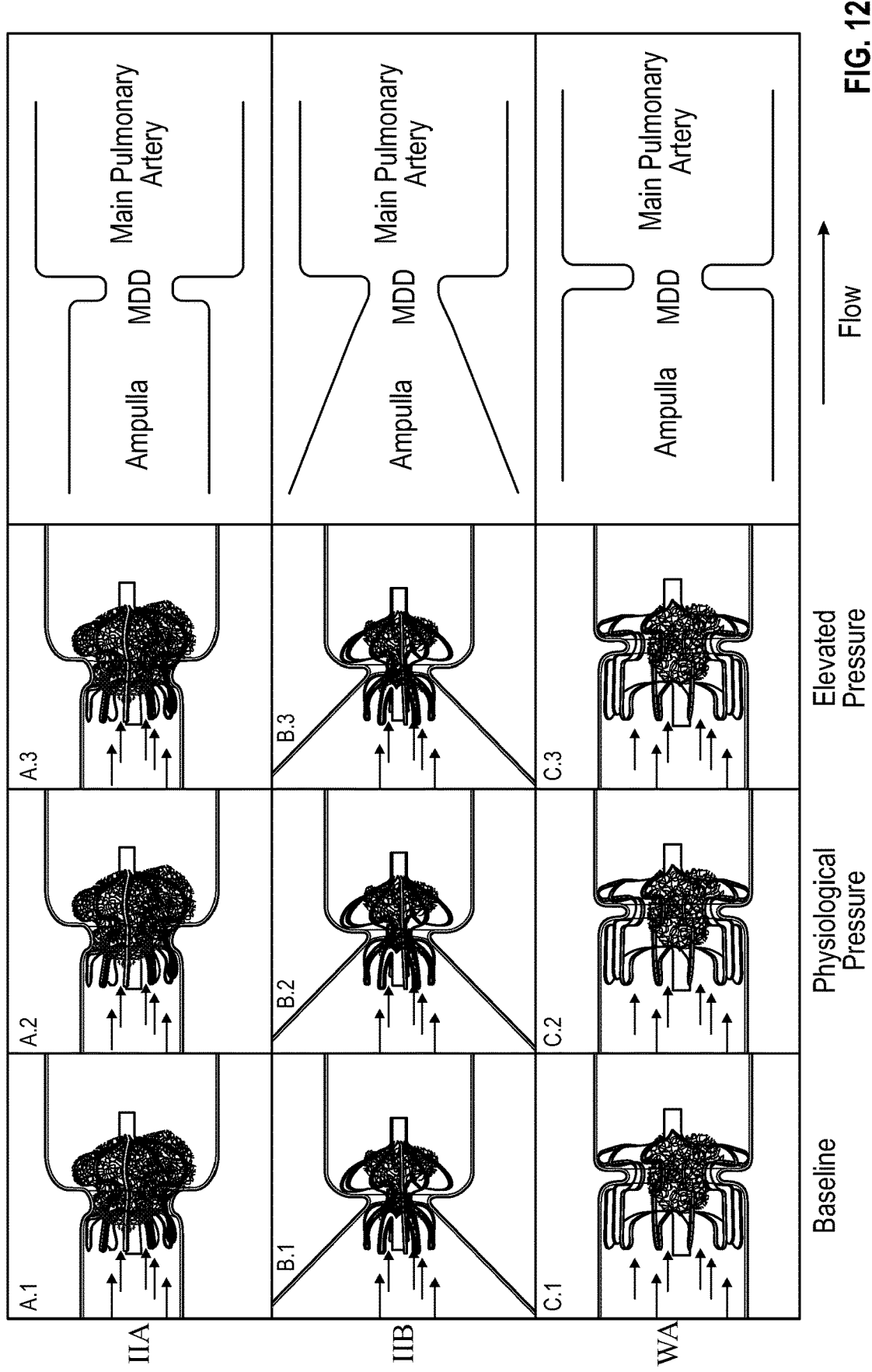
FIG. 12 is an exemplary process according to an embodiment.

For example, see FIG. 12 (A.3).

In another version of Example 9a the second proximal configuration has a maximum outer diameter that is less than or equal to a maximum outer diameter of the second distal configuration Example 10a. The system of example 4a, wherein the SMP foam, in the actuated configuration, extends radially from within at least one of the distal and proximal struts respectively in the second proximal and second distal configurations to outside and beyond the at least one of the distal and proximal struts respectively in the second proximal and second distal configurations.

Figure 11:
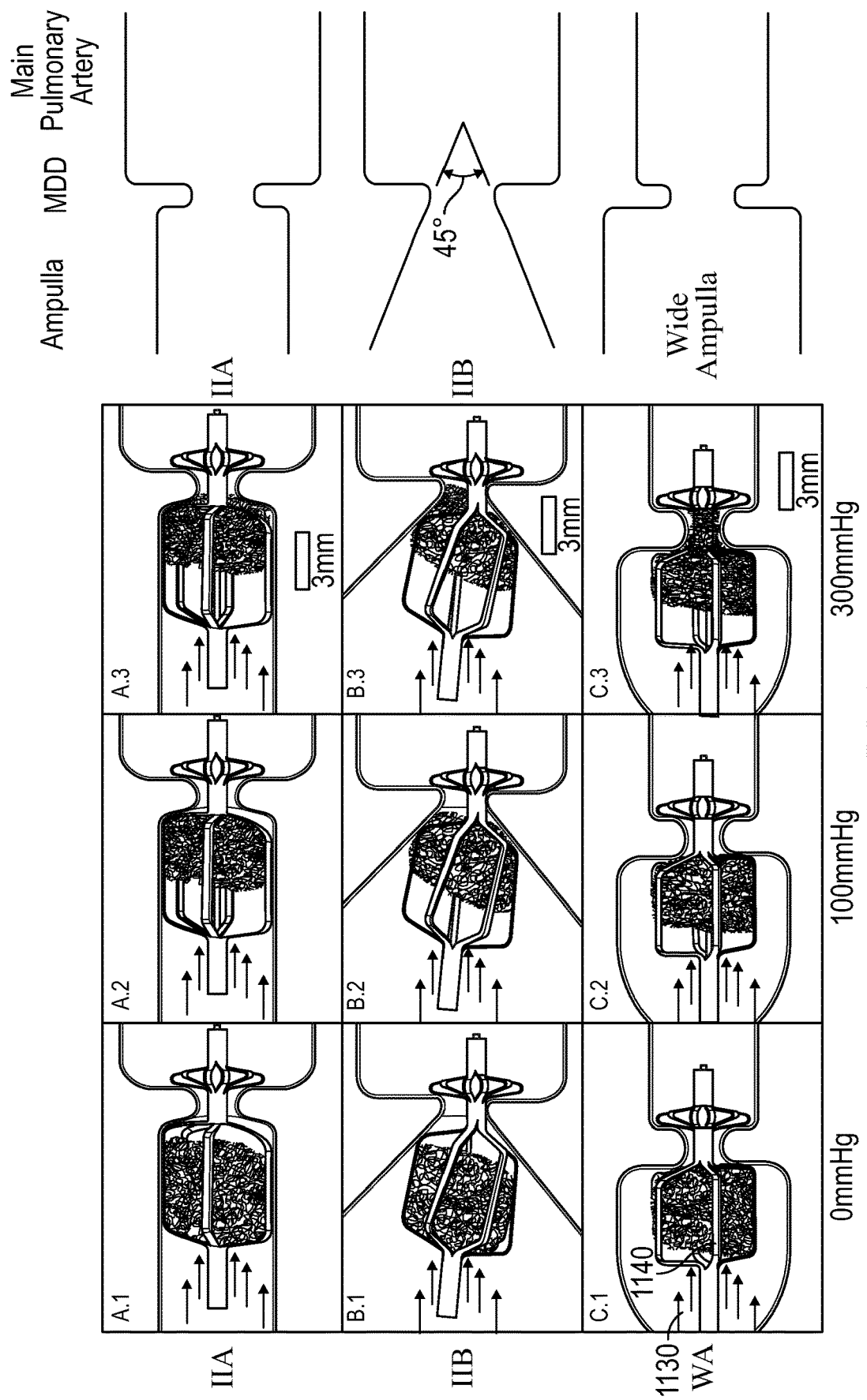
FIG. 11 is an exemplary process according to an embodiment.

For example, See FIG. 12 (A.2) or FIG. 11 (B.3).

Example 11a. The system of example 4a, wherein the SMP foam, in the actuated configuration, extends radially from within the distal struts in the second distal configuration to outside and beyond the distal struts in the second distal configuration.

Example 12a. The system of example 4a comprising a monolithic strut that includes one of the proximal struts and one of the distal struts and which extends through the middle portion.

For example, see FIG. 4.

Example 13a. The system of example 4a, wherein: the SMP foam has a length that extends from a proximal end of the SMP foam to a distal end of the SMP foam; the SMP foam is fixedly attached to the system along only a portion of the length and is not fixedly attached to the system along another portion of the length.

For example, the SMP foam may be 320 of FIG. 3 may fixedly couple to portion 330 but may slideably couple to more distal portions of member 340. In FIG. 11(C.1) to FIG. 11(C.2) notice how the foam slides along member 1140 (although this does not show the foam fixedly attached to, for example, element 1130).

Example 14a. The system of example 13a comprising a central member that is proximal to the middle portion, wherein: the SMP foam includes first and second portions; the first portion is fixedly attached to the first central member; and the second portion is slideably coupled to the central member.

A central member may include, for example, element 1130 of FIG. 11 or element 340 of FIG. 3. In FIG. 11(B.1) the foam is on the proximal portion of backbone 1130 and in FIG. 11 (B.2) the foam is on the distal portion of backbone 1130. Thus, in these two figures the foam is slideably coupled to the backbone and is not fixedly attached to the backbone. However, in other embodiments a portion of the foam may be fixedly attached to the system (e.g., to the backbone or a portion analogous to portion 441 of FIG. 4) and another portion may be slidably coupled to the system (e.g., to the backbone).

Example 15a. The system of example 4a, wherein the SM material is selected from the group comprising: a SM alloy and a SMP.

Example 16a. The system of example 4a, wherein a proximal face of the proximal portion is generally concave in the second proximal configuration with a focus that is proximal to the proximal face.

See, for example, "focus" 430' of FIG. 4. The proximal face of portion 411 is an example of "generally concave." In some embodiments, such as FIG. 2A, the distal element may include a concave proximal face.

Example 17a. The system of example 4a, wherein: the proximal portion includes a proximal most end and the distal portion includes a distal most end; the proximal most end is monolithic with the proximal struts and the proximal struts terminate at a distal portion of the proximal most end; and the distal most end is monolithic with the distal struts and the distal struts terminate at a proximal portion of the distal most end.

For example, see ends 442 and 441 of FIG. 4.

Example 18a. The system of example 1a comprising: an additional conduit comprising: (c)(i) an additional proximal portion including additional proximal struts, (c)(ii) an additional distal portion including additional distal struts, and (c)(iii) an additional middle portion coupling the additional proximal struts to the additional distal struts; and an additional SMP foam; wherein (d)(i) the additional proximal and additional distal struts include the SM material, (d)(ii) the additional proximal struts expand from an additional first proximal configuration to an additional second proximal configuration and the additional distal struts expand from an additional first distal configuration to an additional second distal configuration; (d)(iii) the additional second proximal configuration has a larger maximum outer diameter than the additional first proximal configuration; and (d)(iii) the additional SMP foam is included within the additional proximal struts when the additional proximal struts are in the additional second proximal configuration; wherein the conduit includes a maximum outer diameter when the proximal and distal struts are in the first proximal configuration and the first distal configuration; wherein the additional conduit includes a maximum outer diameter when the additional proximal and distal struts are in the additional first proximal configuration and the additional first distal configuration; wherein the maximum outer diameter of the conduit is equal to the maximum outer diameter of the additional conduit and the maximum outer diameter of the additional second proximal configuration is larger than the maximum outer diameter of the second proximal configuration.

For example, two tubes or conduits of equal outer diameter (and possibly equal length in some embodiments but not in others) may be treated differently to form devices with different maximum diameters. For example a first tube may have shorter slits formed in it than a second tube. After the SMA struts are set, the longer struts may have a greater outer diameter (once expanded) than the shorter struts of the first tube. This provides efficiencies in manufacturing whereby the same conduits (or at least conduits having the same initial outer diameter) form different devices (devices having larger maximum deployed diameters such as diameters 212' and 211' of FIG. 2A) based on the formation of longer slits/struts. In some embodiments, to accommodate significantly longer struts the tubes may have the same initial outer diameters but different overall lengths).

Example 19a. The system of example 1a comprising an intravascular pusher rod detachably coupled to the conduit.

For example, the pusher rod may be threaded and couple to element 230 of FIG. 2A. However, other decoupling mechanisms may be used such as, for example, electrolytic release and the like. A pusher rod may include any cable or member that is stiff enough to be used to push the device out of a delivery conduit (e.g., sheath) and/or withdraw the device from an anatomic anomaly and/or into the delivery conduit.

Example 20a. The system of example 1a comprising an additional SMP foam included within the distal struts when the distal struts are in the second distal configuration, wherein the SMP foam is not monolithic with the additional SMP foam.

For example, see FIG. 4, elements 421, 422.

Example 21a. The system of example 1a, wherein in the second proximal configuration a proximal portion of a first strut included in the proximal struts is collinear with a wall of the conduit and another portion of the first strut is not collinear with the wall of the conduit.

For example, in FIG. 13A the most proximal portion of the strut is collinear with the proximal wall of the conduit but other portions of the strut (e.g., midway along the strut forming the proximal cage) the strut is obviously deployed/expanded with an expanded diameter that places the strut in a non-collinear arrangement with the proximal wall of the conduit. Doing so increases fatigue life for the struts. To manufacture such a configuration, the collinear portions addressed above may be purposefully constrained during the shaping process (e.g., by placing a collar over the strut portion and conduit tube one wishes to remain collinear with each other. Using the collars bypasses the stress concentrations that would occur during bending of struts that are formed at the interface where the strut connects to the tube. The collinear portion of the strut allows for better torsion and angling of the cages to fit into the expanded strut geometries (e.g., concave and the like) as well.

In an embodiment in the second distal configuration a distal portion of the strut is collinear with a wall of the conduit (e.g., distal wall) and another portion of the strut is not collinear with the wall (e.g., distal wall) of the conduit. See, for example, FIG. 13A.

Example 22a. A system comprising: a conduit with proximal and distal struts that comprise a wall of the conduit, the proximal and distal struts each including a shape memory (SM) material; and a shape memory polymer (SMP) foam; wherein (a)(i) the proximal struts are configured to expand to form a proximal cage and the distal struts are configured to expand to form a distal cage; and (a)(ii) the SMP foam is configured to be, in an unactuated state, included in at least one of the proximal and distal cages.

For example, see FIGS. 13A and 13B. The struts may be, for example, SMP or SMA. The SMP foam may be a monolithic piece that extends from the proximal cage to the distal cage or may be, for example, separate foams with one of the foams in the proximal cage and another in the distal cage.

Example 23a. The system of example 22a, wherein the proximal and distal struts are monolithic with each other.

Example 24a. The system of example 23a, wherein the proximal and distal cages are separated from each other by a narrow portion of the conduit that has a smaller maximum diameter than either of the proximal and distal cages.

Example 25a. The system of example 24, wherein the SMP foam is a monolithic foam included in the proximal and distal cages.

Thus, embodiments provide numerous advantages.

An embodiment includes a cupped shape (e.g., see portion 411 of FIG. 4). This shape provides a form of stepped locking mechanism that helps lock the device in place upon deployment and also guides the device back into the catheter when recapturing the device. For example, the concave portions provide points of rotation whereby portion 441 is withdrawn into a lumen first. Portion 441 pulls on portion 411 forming a conical section with the tip of the cone being withdrawn into the lumen first. The concave aspect of portion 411 facilitates the formation of the cone.

Further, conically shaped distal portions may foster a lower profile for the device, thereby allowing for smaller inner diameter lumens for device deployment. More specifically, in an embodiment the distal portion is flat upon full deployment (e.g., see generally flat proximal face of distal portion 412 of FIG. 12) but the distal portion 412 may be conical in shape during deployment. Thus, portion 412 has an intermediate conical shape that is formed during deployment and is present because the still compressed waist struts constrain the distal struts such that they cannot fully expand.

Radiopaque marker bands may be added at, for example, proximal and distal ends of the device. If the design allows (monolithic with two distinct cages separated by a portion of uncut tubing (waist), such as FIG. 1A) a marker band could be placed over the waist/between the two cages.

A threaded mechanism (e.g., area 130) may be located within the proximal stem of an embodiment and attach to a delivery cable (i.e., pusher rod).

Further, a delivery system profile (i.e., compressed device diameter) is determined by the outer diameter of the tube from which the struts are formed (or from the compressed diameter of the SMP foam). The advantages of this are discussed with regard to Example 18a. Regarding Example 18a, please note embodiments provide a "semi-modular" design in that shapes of each portion (proximal, waist, and distal) can be changed independently of each other based on the application and vessel morphology it is designed to fit within. By just changing the length of the laser cut struts, the diameter of the cages can be increased or decreased (this is how device size can be changed while preserving the low delivery system profile), or one can change the fixturing (e.g., mold used to set the SMA strut expanded configuration) and make a completely different cage shape for any portion, while keeping the others the same.

Although the present invention has been described in terms of specific embodiments, it is anticipated that alterations and modifications thereof will become apparent to those skilled in the art. Therefore, it is intended that the following claims be interpreted as covering all such alterations and modifications as fall within the true spirit and scope of the invention.

What is claimed is:

1. A system comprising:
 a cage with proximal and distal strut portions, the proximal and distal strut portions each including a shape memory (SM) material; and
 a contiguous single-piece shape memory polymer (SMP) foam including first and second foam portions;
 wherein (a) the proximal strut portions are configured to expand to form a proximal cage portion and the distal strut portions are configured to expand to form a distal cage portion; and (b) the SMP foam is included in at least one of the proximal or distal cage portions; and
 wherein the first foam portion is configured to slide (a) within the at least one of the proximal or distal cage portions, and (b) towards the second foam portion;
 wherein the proximal and distal cage portions are joined together at a cage location that has a smaller maximum diameter than at least one of the proximal or distal cage portions.

2. The system of claim 1, wherein the proximal and distal strut portions are monolithic with each other.

3. The system of claim 1 comprising a central member, wherein:
 the second foam portion is fixedly attached to the central member;
 the first foam portion is slidably coupled to the central member;
 the central member includes a long axis;
 the first foam portion surrounds the central member in a first plane, the first plane being orthogonal to the long axis; and
 the second foam portion surrounds the central member in a second plane, the second plane being orthogonal to the long axis.

4. The system of claim 1, wherein the first foam portion is configured to slide (a) within the at least one of the proximal or distal cage portions, and (b) towards the second foam portion while the second foam portion remains fixed within at least one of the at least one of the proximal or distal cage portions or another of the at least one of the proximal or distal cage portions.

5. The system of claim 1, wherein:
 the first foam portion is proximal to the second foam portion; and
 the SMP foam is configured to be, in an unactuated state, included in at least one of the proximal or distal cage portions.

6. An occlusion system for a tissue void, the system comprising:
 a frame comprising: (a) a proximal structure portion including proximal strut portions, and (b) a distal structure portion including distal strut portions;
 a shape memory polymer (SMP) foam that expands from an unactuated configuration to an actuated configuration; and
 a central member that is at least partially proximal to the distal structure portion and which is included in at least one of the proximal or distal structure portions;
 wherein (a) the proximal and distal strut portions include a shape memory (SM) material, (b) the proximal strut portions expand from a first proximal configuration to a second proximal configuration and the distal strut portions expand from a first distal configuration to a second distal configuration, (c) the second proximal configuration has a larger maximum outer diameter than the first proximal configuration and the second distal configuration has a larger maximum outer diameter than the first distal configuration, (d) the second proximal configuration has a larger maximum outer diameter than the second distal configuration, and (e) the SMP foam is, in the unactuated configuration, included within a proximal space defined by the proximal strut portions when the proximal strut portions are in the second proximal configuration;
 wherein (a) the SMP foam has a length that extends from a proximal end of the SMP foam to a distal end of the SMP foam; and (b) the SMP foam is fixedly attached to the central member along only a second portion of the length and is slidably coupled to the central member along a first portion of the length.

7. The system of claim 6, wherein the SMP foam, in both the unactuated and actuated configurations, is included within each of: (a) the proximal space defined by the proximal strut portions when the proximal strut portions are in the second proximal configuration, and (b) a distal space defined by the distal strut portions when the distal strut portions are in the second distal configuration.

8. The system of claim 6, wherein the SMP foam, in the actuated configuration, extends radially from within at least one of the at least one of the proximal or distal structure portions to outside and beyond the at least one of the at least one of the proximal or distal structure portions.

9. A system comprising:
a cage comprising: (a) a proximal cage portion including proximal strut portions, and (b) a distal cage portion including distal strut portions; and
a monolithic shape memory polymer (SMP) foam that expands from an unactuated configuration to an actuated configuration;
wherein (a) the proximal and distal strut portions include a shape memory (SM) material, (b) the proximal strut portions expand from a first proximal configuration to a second proximal configuration and the distal strut portions expand from a first distal configuration to a second distal configuration, (c) the second proximal configuration has a larger maximum outer diameter than the first proximal configuration and the second distal configuration has a larger maximum outer diameter than the first distal configuration, and (d) the SMP foam is included within a proximal space defined by the proximal strut portions when the proximal strut portions are in the second proximal configuration;
wherein (a) the SMP foam is not fixedly and directly connected to either of the proximal or distal strut portions, and (b) the SMP foam is configured to expand from the unactuated configuration to the actuated configuration independently from either of the proximal or distal strut portions.

10. The system of claim 9, wherein the SMP foam is, in the unactuated configuration, included within a distal space defined by the distal strut portions when the distal strut portions are in the second distal configuration.

11. The system of claim 9, wherein the SMP foam, in both the unactuated and actuated configurations, is included within the proximal space defined by the proximal strut portions when the proximal strut portions are in the second proximal configuration and a distal space defined by the distal strut portions when the distal strut portions are in the second distal configuration.

12. The system of claim 9, wherein:
in the second proximal configuration the proximal strut portions form an expanded proximal cage portion and in the second distal configuration the distal strut portions form an expanded distal cage portion; and
the SMP foam, in the actuated configuration, extends radially from within at least one of the expanded proximal or distal cage portions to outside and beyond the at least one of the expanded proximal or distal cage portions.

13. The system of claim 12, wherein the SMP foam, in the actuated configuration, is configured to fill a majority of the at least one of the expanded proximal or distal cage portions.

14. The system of claim 9, wherein:
in the second proximal configuration the proximal strut portions form an expanded proximal cage portion and in the second distal configuration the distal strut portions form an expanded distal cage portion; and
the SMP foam, in the actuated configuration, is configured to fill a majority of at least one of the expanded proximal or distal cage portions.

15. The system of claim 9, wherein the SMP foam, in the actuated configuration, extends radially from within a distal space defined by the distal strut portions in the second distal configuration to outside and beyond the distal strut portions in the second distal configuration.

16. The system of claim 9 comprising a central member that is at least partially proximal to the distal cage portion, wherein:
the SMP foam includes first and second foam portions;
the first foam portion is fixedly attached to the central member; and
the second foam portion is slidably coupled to the central member.

17. The system of claim 9 wherein the SMP foam is, in the unactuated configuration, included within the proximal space defined by the proximal strut portions when the proximal strut portions are in the second proximal configuration.

* * * * *